US008470340B2

(12) United States Patent
Beernink et al.

(10) Patent No.: US 8,470,340 B2
(45) Date of Patent: Jun. 25, 2013

(54) PEPTIDES PRESENTING AN EPITOPE OF A DOMAIN OF FACTOR H BINDING PROTEIN AND METHODS OF USE

(75) Inventors: Peter Beernink, Oakland, CA (US); Franco Felici, Campobasso (IT); Dan M. Granoff, Berkeley, CA (US)

(73) Assignees: Children's Hospital & Research Center Oakland, Oakland, CA (US); Novartis Vaccines and Diagnostics, SRL, Siena (IT); Universita degli Studi del Molise, Campobasso (IT)

( * ) Notice: Subject to any disclaimer, the term of this patent is extended or adjusted under 35 U.S.C. 154(b) by 0 days.

(21) Appl. No.: 13/058,283

(22) PCT Filed: Sep. 2, 2009

(86) PCT No.: PCT/US2009/055795
§ 371 (c)(1),
(2), (4) Date: Apr. 7, 2011

(87) PCT Pub. No.: WO2010/028096
PCT Pub. Date: Mar. 11, 2010

(65) Prior Publication Data
US 2011/0318378 A1    Dec. 29, 2011

Related U.S. Application Data

(60) Provisional application No. 61/094,041, filed on Sep. 3, 2008.

(51) Int. Cl.
*A61K 39/095* (2006.01)
*A61K 39/02* (2006.01)
*A61K 39/00* (2006.01)
*A61K 38/00* (2006.01)
*C07K 1/00* (2006.01)

(52) U.S. Cl.
USPC ............... 424/250.1; 424/190.1; 424/234.1; 424/184.1; 514/1.1; 530/300; 530/350; 530/825; 530/806

(58) Field of Classification Search
None
See application file for complete search history.

(56) References Cited

U.S. PATENT DOCUMENTS

| 6,030,619 A | 2/2000 | Granoff et al. |
|---|---|---|
| 2006/0029621 A1 | 2/2006 | Granoff et al. |
| 2009/0035328 A1 | 2/2009 | Granoff |

FOREIGN PATENT DOCUMENTS

| WO | 9957280 | 11/1999 |
|---|---|---|
| WO | 0134642 | 5/2001 |
| WO | 2004048404 | 6/2004 |
| WO | 2006081259 | 8/2006 |
| WO | 2009114485 | 9/2009 |

OTHER PUBLICATIONS

Beernink, et al. "Use of Phage Display to Identify a Conserved Region of Factor H-Binding Protein That Affects the Epitope of a Protective, Cross-Reactive mAb" International Pathogenic Neisseria Conference, Rotterdam, Sep. 7, 2008.
Beernink, et al. "Use of Phage Display to Identify a Conserved Region of the a Domain of Factor H Binding Protein (fhbp) that Affects Epitope Expression of a Protective Cross-Reactive mAb" International Pathogenic Neisseria Conference, Rotterdam, Sep. 7, 2008.
Beernink, et al. (2007) "Prevalence of Factor H-Binding Protein Variants and NadA among Meningococcal Group B Isolates from the United States: Implications for the Development of a Multicomponent Group B Vaccine" J. Infect. Dis. 195(10):1472-1479.
Borrow, et al. (2001) "Serological Basis for Use of Meningococcal Serogroup C Conjugate Vaccines in the United Kingdom: Reevaluation of Correlates of Protection" Infect. Immun. 69(3):1568.
Cantini, et al. (2009) "Solution Structure of the Factor H-binding Protein, a Survival Factor and Protective Antigen of *Neisseria meningitidis*" J. Biol. Chem. 284(14:9022-9026.
Fisseha, et al. (2005) "Characterization of Native Outer Membrane Vesicles from IpxL Mutant Strains of *Neisseria meningitidis* for Use in Parenteral Vaccination" Infect. Immun. 73(7):4070-4080.
Fletcher, et al. (2004) "Vaccine Potential of the *Neisseria meningitidis* 2086 Lipoprotein" Infect. Immun. 72 (4):2088-2100.
Giuliani, et al. (2006) "A Universal Vaccine for Serogroup B Meningococcus" PNAS USA 103(29):10834-10839.
Giuliani, et al. (2005) "The Region Comprising Amino Acids 100 to 255 of *Neisseria meningitidis* Lipoprotein GNA 1870 Elicits Bactericidal Antibodies" Infect Immun. 73(2):1151-1160.
Goldschneider, et al. (1969) "Human Immunity to the Meningococcus: I. The Role of Humoral Antibodies" J. Exp. Med. 129(6):1307-1326.
Granoff, et al. (2001) "A Novel Mimetic Antigen Eliciting Protective Antibody to *Neisseria meningitidis*" J. Immunol. 167(11):6487-6496.
Lowell, et al. (1988) "Peptides Bound to Proteosomes via Hydrophobic Feet Become Highly Immunogenic without Adjuvants" J. Exp. Med. 167(2):658-663.
Mascioni, et al. (2009) "Structural Basis for the Immunogenic Properties of the Meningococcal Vaccine Candidate LP2086" J. Biol. Chem. 284(13):8738-8746.
Masignani, et al. (2003) "Vaccination against *Neisseria meningitidis* Using Three Variants of the Lipoprotein GNA1870" Exp. Med. 197(6):789-799.
Moe, et al. (2002) "Sequential Immunization with Vesicles Prepared from Heterologous *Neisseria meningitidis* Strains Elicits Broadly Protective Serum Antibodies to Group B Strains" Infect. Immun. 70(11):6021-6031.
Ram, et al. (1998) "A Novel Sialic Acid Binding Site on Factor H Mediates Serum Resistance of Sialylated *Neisseria gonorrhoeae*" J. Exp. Med. 187(5):743-752.
Schneider, et al. (2009) "*Neisseria meningitidis* Recruits Factor H Using Protein Mimicry of Host Carbohydrates" Nature 458(7240):890-893.

(Continued)

*Primary Examiner* — S. Devi
(74) *Attorney, Agent, or Firm* — Carol L. Francis; Bozicevic, Field & Francis LLP

(57) ABSTRACT

Polypeptides that can elicit antibodies that are bactericidal for different fHbp variant strains of *N. meningitidis*, and methods of use, are provided.

40 Claims, 9 Drawing Sheets

OTHER PUBLICATIONS

Steeghs, et al. (1999) "Immunogenicity of Outer Membrane Proteins in a Lipopolysaccharide-Deficient Mutant of *Neisseria meningitidis*: Influence of Adjuvants on the Immune Response" Infect. Immun. 67(10):4988-4993.

Steeghs, et al. (2004) "Teasing Apart Structural Determinants of 'Toxicity' and 'Adjuvanticity': Implications for Meningococcal Vaccine Development" J. Endotoxin. Res.10(2):113-119.

Van Der Ley, et al. (2001) "Modification of Lipid A Biosynthesis in *Neisseria meningitidis* IpxL Mutants: Influence on Lipopolysaccharide Structure, Toxicity, and Adjuvant Activity" Infect. Immun. 69(10):5981-5990.

Welsch, et al. (2004) "Protective Activity of Monoclonal Antibodies to Genome-Derived Neisserial Antigen 1870, a *Neisseria meningitidis* Candidate Vaccine" J. Immunol. 172(9):5606-5615.

Beernink & Granoff (2008) "Bactericidal Antibody Responses Induced by Meningococcal Recombinant Chimeric Factor H-Binding Protein Vaccines" Infect Immun. 76(6):2568-2575.

Beernink, et al. (2008) "Fine Antigenic Specificity and Cooperative Bactericidal Activity of Monoclonal Antibodies Directed at the Meningococcal Vaccine Candidate, Factor H-Binding Protein" Infect Immun. 76(9):4232-4240.

Beernink, et al. (2009) "A Region of the N-Terminal Domain of Meningococcal Factor H-Binding Protein that elicits Bactericidal Antibody across Antigenic Variant Groups" Mol. Immunol. 46(8-9):1647-1653.

Beernink, et al. (2009) "The Modular Architecture of Meningococcal Factor H-Binding Protein" Microbiology 155(Pt. 9):2873-2883.

Welsch, et al. (2008) "Complement-Dependent Synergistic Bactericidal Activity of Antibodies against Factor H-Binding Protein, a Sparsely Distributed Meningococcal Vaccine Antigen" J. Infect. Dis. 197(7):1053-1061.

Felici, et al. (1993) "Mimicking of Discontinuous Epitopes by Phage-Displayed Peptides, II. Selection of clones recognized by a Protective Monoclonal Antibody against the *Bordetella pertussis* Toxin from Phage Peptide Libraries" Gene 128(1):21-27.

GenBank: AAS56915.1 "Lipoprotein GNA1870 [*Neisseria meningitidis*]" dated Apr. 22, 2004.

GenBank: AAS56916.1 "Lipoprotein GNA1870 [*Neisseria meningitidis*]" dated Apr. 22, 2004.

GenBank: AAS56917.1 "Lipoprotein GNA1870 [*Neisseria meningitidis* M6190]" dated Apr. 22, 2004.

GenBank: AAS56918.1 "Lipoprotein GNA1870 [*Neisseria meningitidis*]" dated Apr. 22, 2004.

GenBank: AAS56919.1 "Lipoprotein GNA1870 [*Neisseria meningitidis*]" dated Apr. 22, 2004.

GenBank: AAS56920.1 "Lipoprotein GNA1870 [*Neisseria meningitidis*]" dated Apr. 22, 2004.

GenBank: AAT01289.1 "Lipoprotein [*Neisseria meningitidis* H44/76]" dated May 1, 2004.

GenBank: AAT01290.1 "Lipoprotein [*Neisseria meningitidis* CU385]" dated May 1, 2004.

GenBank: AY548370.1 "*Neisseria meningitidis* Strain H44/76 Lipoprotein (gna1870) Gene, Complete cds" dated May 1, 2004.

GenBank: AY548371.1 "*Neisseria meningitidis* Strain CU385 Lipoprotein (gna1870) Gene, Complete cds" dated May 1, 2004.

GenBank: AY548372.1 "*Neisseria meningitidis* Strain BZ83 Lipoprotein GNA1870 (gna1870) Gene, Complete cds" dated Apr. 22, 2004.

GenBank: AY548373.1 "*Neisseria meningitidis* Strain 4243 Lipoprotein GNA1870 (gna1870) Gene, Complete cds" dated Apr. 22, 2004.

GenBank: AY548374.1 "*Neisseria meningitidis* Strain M6190 Lipoprotein GNA1870 (gna1870) Gene, Complete cds" dated Apr. 22, 2004.

GenBank: AY548375.1 "*Neisseria meningitidis* Strain N98/254 Lipoprotein GNA1870 (gna1870) Gene, Complete cds" dated Apr. 22, 2004.

GenBank: AY548376.1 "*Neisseria meningitidis* Strain M1390 Lipoprotein GNA1870 (gna1870) Gene, Complete cds" dated Apr. 22, 2004.

GenBank: AY548377.1 "*Neisseria meningitidis* Strain M4105 Lipoprotein GNA1870 (gna1870) Gene, Complete cds" dated Apr. 22, 2004.

GeneID: 904318; NCBI Reference Sequence: NP_274866.1 "Hypothetical Protein NMB1870 [*Neisseria meningitidis* MC58]" dated Apr. 22, 2004.

Gershoni et al. (2007) "Epitope Mapping—The First Step in Developing Epitope-Based Vaccines" BioDrugs 21 (3):145-156.

Koeberling et al. (2008) "Bactericidal Antibody Responses Elicited by a Meningococcal Outer Membrane Vesicle Vaccine with Overexpressed Factor H-Binding Protein and Genetically Attenuated Endotoxin" J Infect Dis 198 (2):262-270.

Meola, et al. (1995) "Derivation of Vaccines from Mimotopes: Immunologic Properties of Human Hepatitis B Virus Surface Antigen Mimotopes Displayed on Filamentous Phage" J. Immunol. 154(7):3162-3172.

Figure 1

```
 | ←--leader----→|
MNRTAFCCLSLTTALILTA                                                  -19

| ←------------------ A Domain ------------------------------→
CSSGGGGVAADIGAGLADALTAPLDHKDKGLQSLTLDQSVRKNEKLKIAAQGAEKTYGNGDSLNTGK    67
↑
+1
optionally lipidated ←---A Domain------------------  ←--------B Domain-------→
LKNDKVSRFDFIRQIEVDGQLITLESGEFQVYK QSHSALTAFQTEQIQDSEHSGKMVAKR          127
                                 ↑                 αααααααα
                                101                AH1

←--------B Domain----------------→| ←--------C Domain-->
QFRIGDIAGEHTSFDKLPEGGRATYRGTAFGSDDAGG KLTYTIDFAAKQGNGKIEHLKSP          187
        αααααααα                    ↑
          AH2                      164

←---------------------------C Domain--------------------→
ELNVDLAAADIKPDGKRHAVISGSVLYNQAEKGSYSLGIFGGKAQEVAGSAEVKTVNGIR           247

←------→|
HIGLAAKQ                                                              255
```

Fig. 2

| Murine anti-fHBP monoclonal antibodies | | | |
|---|---|---|---|
| JAR MAb (Immunogen[1]) | Reactivity Across Variants (ELISA)[2] | Ig Isotype | Inhibits binding of fH[3] |
| (rfHBP v.1) | | | |
| 1 | v.1 (subset) | G3 | Yes |
| 3 | v.1 (nearly all) | G3 | Yes |
| 4 | v.1, v.2 (high reactivity) and v.3 (lower reactivity) | G2a | No |
| 5 | v.1 (nearly all) | G2b | Yes |
| (rfHBP v.2) | | | |
| 10 | v.1 (subset), v.2 (subset) and v. 3 (subset) | G1 | No |
| 11 | v.2 (subset) and v.3 (subset) | G2a | Partial |
| 13 | v. 2 (subset) and v.3 (all) | G2a | Yes |
| (rfHBP v.3) | | | |
| 32 | v. 3 and v.2 (subset) | G2a | Yes |
| 33 | v. 3 and v.2 (subset) | G2a | No |
| 35 | v.3 and v.2 (subset) | G2b | Yes |
| 36 | v.3 and v.2 (nearly all) | G2b | Partial |

[1] Mice were immunized with recombinant proteins expressed from the genes from *N. meningitidis* strains MC58 (v.1), 2996 (v.2) and M1239 (v.3). All MAbs show evidence of synergistic complement-mediated bactericidal activity when tested with a second MAbs (See Figure 18), which is evidence of recognition of surface-accessible epitopes.

[2] With exception of JAR 4, the results are based on antibody binding to bacterial cells from different strains as measured by ELISA and identification of their respective fHBP variant groups by RT-PCR (Beernink et al., Clin Vacc Immunol 2006 13(7):758-763). The JAR 4 cross-reactivity is based on binding to purified recombinant proteins in an ELISA and flow cytometry with live bacterial cells (Welsch et al J Immunol 2004 172:5606-5615).

[3] Based on inhibition of binding of purified human fH to rfHBP by ELISA in the presence of JAR anti-fHBP mAb (see representative data in Figure 19).

```
MC58  21 TAPLDHKDKG 30 (SEQ ID NO: 64)
D25A  21 TAPLAAKDKG 30 (SEQ ID NO: 65)
H26A  21 TAPLDAKDKG 30 (SEQ ID NO: 66)
K27A  21 TAPLDHADKG 30 (SEQ ID NO: 67)
```

B

```
v.1  1 CSSGGGG--- --VAADIGAG LADAL    20
v.2  1 CSSGGGG--- --VAADIGAG LADAL    20
v.3  1 CSSGGGGSGG GGVAADIGTG LADAL    25
       *****       *** * ***** v.1 21 TAPLDHKDKG LQSLTLDQSV          40
v.2 21 TAPLDHKDKS LQSLTLDQSV          40
v.3 26 TAPLDHKDKG LKSLTLEDSI          45
       *********  * ****  * v.1 41 RKNEKLKLAA QGAEKTYGNG D---     60 (SEQ ID NO: 68)
v.2 41 RKNEKLKLAA QGAEKTYGNG D---     60 (SEQ ID NO: 69)
v.3 41 PQNGTLTLSA QGAEKTFKAG DKDN     69 (SEQ ID NO: 70)
        *  *  *   ******   * *
```

*Conserved in fHbp v.1, v.2 and v.3

Fig. 8

| Clone number | Amino acid sequence | Nucleotide sequence |
|---|---|---|
| 1. | H D H K L E G T E (SEQ ID NO: 14) | CACGATCATAAATTAGAAGGCACGGAG (SEQ ID NO: 45) |
| 2. | C G G V Y D D K T G C A (SEQ ID NO: 15) | TGTGGCGGGGTCTACGACGACAAGACGGGGTGTGCG (SEQ ID NO: 46) |
| 3. | H D H K T Q L D P (SEQ ID NO: 16) | CATGACCACAAGACCCAGCTCGACCCG (SEQ ID NO: 47) |
| 4. | W T L A V F D H K A Q T (SEQ ID NO: 17) | TGGACCCTGGCGGTGTTCGACCACAAAGCGCAGACC (SEQ ID NO: 48) |
| 5. | G C M G Y D H R S G C V (SEQ ID NO: 18) | GGGTGTATGGGCTACGACCACAGGTCGGGCTGTGTG (SEQ ID NO: 49) |
| 6. | F H D H K T A N Q (SEQ ID NO: 19) | TTTCATGACCACAAAACTGCCAATCAG (SEQ ID NO: 50) |
| 7. | W R W C G F E R C P E G (SEQ ID NO: 20) | TGGAGGTGGTGTGGCTTCGAGCGCTGTCCCGAGGGC (SEQ ID NO: 51) |
| 8. | H D H R I W P L D V T A (SEQ ID NO: 21) | CACGACCACCGTATCTGGCCGCTGGACGTGACCGCG (SEQ ID NO: 52) |
| 9. | N D E R Q M S D W Y R A (SEQ ID NO: 22) | AACGACGAACGTCAGATGTCCGACTGGTACCGTGCG (SEQ ID NO: 53) |
| 10. | H V H R G S Q G G Q R Q (SEQ ID NO: 23) | CACGTCCACCGTGGTTCGCAGGGTGGTCAGCGTCAG (SEQ ID NO: 54) |
| 11. | L E W C G F S R C E V G (SEQ ID NO: 24) | CTCGAGTGGTGTGGCTTCAGCAGGTGTGAGGTCGGC (SEQ ID NO: 55) |
| 12. | K D H R H M L W P E E S (SEQ ID NO: 25) | AAAGACCACCGTCACATGCTGTGGCCGGAAGAATCC (SEQ ID NO: 56) |
| 13. | L C Q E R L S q R C G V (SEQ ID NO: 26) | CTCTGTCAGGAGCGGCTCTCCTAGAGGTGTGGGGTG (SEQ ID NO: 57) |
| 14. | W V L C G q G C G G T A (SEQ ID NO: 27) | TGGGTGTTGTGTGGCTAGGGCTGTGGGGCACGGCG (SEQ ID NO: 58) |
| 15. | R C q V Q V M V L C A L (SEQ ID NO: 28) | AGGTGTTAGGTCCAGGTCATGGTGCTGTGTGCGCTC (SEQ ID NO: 59) |
| 16. | H D H K H G F Q E P A S (SEQ ID NO: 29) | CACGACCACAAACACGGTTTCCAGGAACCGGCGTCC (SEQ ID NO: 60) |
| 17. | S D W G W G G R A E Q H (SEQ ID NO: 30) | TCCGACTGGGGTTGGGGTGGCCGTGCGGAACAGCAC (SEQ ID NO: 61) |
| 18. | V G W C G F E R C S S A (SEQ ID NO: 31) | GTGGGGTGGTGTGGCTTCGAGCGGTGTTCGTCGGCG (SEQ ID NO: 62) |

PEPTIDES PRESENTING AN EPITOPE OF A DOMAIN OF FACTOR H BINDING PROTEIN AND METHODS OF USE

CROSS-REFERENCE TO RELATED APPLICATION

This application claims priority benefit of U.S. provisional application Ser. No. 61/094,041, filed Sep. 3, 2008, which application is incorporated herein by reference in its entirety.

STATEMENT REGARDING FEDERALLY SPONSORED RESEARCH

This invention was made with government support under National Institutes of Health grant nos. R01 AI46464 and C06 RR16226. The government has certain rights in this invention.

FIELD OF THE INVENTION

This invention relates to antigenic compositions that find use in vaccines for diseases caused by *Neisseria meningitidis*.

BACKGROUND

*Neisseria meningitidis* is a Gram-negative bacterium which colonizes the human upper respiratory tract and is responsible for worldwide sporadic and cyclical epidemic outbreaks of, most notably, meningitis and sepsis. The attack and morbidity rates are highest in children under 2 years of age. Like other Gram-negative bacteria, *Neisseria meningitidis* typically possess a cytoplasmic membrane, a peptidoglycan layer, an outer membrane which together with the capsular polysaccharide constitute the bacterial wall, and pili, which project into the outside environment. Encapsulated strains of *Neisseria meningitidis* are a major cause of bacterial meningitis and septicemia in children and young adults. The prevalence and economic importance of invasive *Neisseria meningitidis* infections have driven the search for effective vaccines that can confer immunity across different strains, and particularly across genetically diverse group B strains with different serotypes or serosubtypes.

Factor H Binding Protein (fHbp, also referred to in the art as lipoprotein 2086 (Fletcher et al, Infect Immun 2004; 72:2088-2100), GNA1870 (Masignani et al. J Exp Med 2003; 197:789-99) or "741") is an *N. meningitidis* protein which is expressed in the bacterium as a surface-exposed lipoprotein. Based on sequence analysis of 71 *N. meningitidis* strains representative of its genetic and geographic diversity, *N. meningitidis* strains have been sub-divided into three fHbp variant groups (referred to as variant 1 (v.1), variant 2 (v.2), and variant 3 (v.3)) based on amino acid sequence variability and immunologic cross-reactivity (Masignani et al. J Exp Med 2003; 197:789-99). Variant 1 strains account for about 60% of disease-producing group B isolates (Masignani et al. 2003, supra). Within each variant group, there is on the order of about 92% or greater conservation of amino acid sequence. Specifically, conservation within each variant group ranges between 89 and 100%, while between the variant groups (e.g., between v.1 and v.2) the conservation can be as low as 59%. The protein is expressed by all known strains of *N. meningitidis*.

Mice immunized with recombinant fHbp developed high serum bactericidal antibody responses against strains expressing fHbp proteins of the homologous variant group (Masignani et al. 2003, supra; Welsch et al. 2004, *J Immunol.* 172(9):5606-15.). Thus, antiserum prepared against fHbp v.1 confers protection against *N. meningitidis* strains expressing fHbp v.1, but not against strains expressing fHbp v.2 or v.3. Similarly, antiserum prepared against fHbp v.2 protects against strains expressing v.2 (or v.3) but not v.1 (Masignani et al. J Exp Med 2003; 197:789-99; Beernink et al. *J Infect Dis* 2007; 195:1472-9).

Vaccines that exploit the ability of fHbp to elicit bactericidal antibody responses and that can elicit such antibodies that are effective against strains expressing different fHbp variants remain of interest.

SUMMARY

Peptides that can elicit antibodies that bind epitopes shared by different fHbp variant strains of *N. meningitidis*, and methods of use.

The present disclosure provides isolated JAR 4 epitope-containing peptides of at least 9 amino acids in length and comprising the sequence:

$DX_1X_2$ wherein
$X_1$ is histidine (H) or aspartic acid (D);
$X_2$ is lysine (K) or arginine (R);
the aspartic acid residue (D) does not contain an N-terminal amino group;
the peptide contains at least 3 amino acid residues positioned immediately C-terminal to $X_2$, wherein the at least 3 amino acid residues are selected from:

| | |
|---|---|
| LEGTE, | (SEQ ID NO: 1) |
| TGCA, | (SEQ ID NO: 2) |
| TQL, | |
| AQT, | |
| SGC, | |
| TANQ, | (SEQ ID NO: 3) |
| IWP, | |
| HML, and | |
| HGF, | | with the proviso that when the at least 3 amino acid residues are TANQ (SEQ ID NO:3), the peptide comprises a histidine (H) immediately N-terminal to the aspartic acid residue (D), and when the at least 3 amino acid residues are TGCA (SEQ ID NO:2), the peptide comprises a tyrosine (Y) immediately N-terminal to the aspartic acid residue (D); the peptide does not comprise a full-length A domain of a factor H binding protein; and the peptide is specifically bound by JAR 4 monoclonal antibody secreted by the hybridoma deposited as ATCC Accession No. PTA-8943.

In related embodiments, the isolated JAR 4 epitope-containing peptide of claim 1, wherein $X_1$ is histidine (H) and $X_2$ is lysine (K). In further embodiments, the isolated JAR 4 epitope-containing peptide of claim 2, wherein the at least 3 amino acid residues are LEGTE (SEQ ID NO: 1), TQL, AQT, TANQ (SEQ ID NO: 3), or HGF. In related embodiments, the isolated JAR 4 epitope-containing peptide of claim 1, wherein $X_1$ is aspartic acid (D) and $X_2$ is lysine (K). In still further embodiments, the isolated JAR 4 epitope-containing peptide of claim 4, wherein the at least 3 amino acid residues are TGCA (SEQ ID NO: 2). In further embodiments, the isolated JAR 4 epitope-containing peptide of claim 1, wherein $X_1$ is histidine (H) and $X_2$ is arginine (R). In related embodiments, the isolated JAR 4 epitope-containing peptide of claim 6, wherein the at least 3 amino acid residues are SGC, IWP, or HML.

The present disclosure also provides peptides of at least 9 amino acids in length and comprising at least 7 contiguous amino acid residues of an amino acid sequence of:

|  |  |
|---|---|
| H D H K L E G T E, | (SEQ ID NO: 14) |
| C G G V Y D D K T G C A, | (SEQ ID NO: 15) |
| H D H K T Q L D P, | (SEQ ID NO: 16) |
| W T L A V F D H K A Q T, | (SEQ ID NO: 17) |
| G C M G Y D H R S G C V, | (SEQ ID NO: 18) |
| F H D H K T A N Q, | (SEQ ID NO: 19) |
| H D H R I W P L D V T A, | (SEQ ID NO: 21) |
| K D H R H M L W P E E S, | (SEQ ID NO: 25) |
| or |  |
| H D H K H G F Q E P A S, | (SEQ ID NO: 29) | wherein the peptide contains DHK, DDK, or DHR, the aspartic acid (D) of DHK, DDK, or DHR does not contain an N-terminal amino group when present at the peptide N-terminus; and the peptide is specifically bound by JAR 4 monoclonal antibody secreted by the hybridoma deposited as ATCC Accession No. PTA-8943.

The present disclosure also provides peptides of at least 9 amino acids in length and comprising a contiguous amino acid sequence of:

|  |  |
|---|---|
| N D E R Q M S D W Y R A, | (SEQ ID NO: 22) |
| or |  |
| H V H R G S Q G G Q R Q. | (SEQ ID NO: 23) |

The present disclosure also provides peptides of at least 9 amino acids in length and comprising a contiguous amino acid sequence of:

|  |  |
|---|---|
| W R W C G F E R C P E G, | (SEQ ID NO: 20) |
| S D W G W G G R A E Q H, | (SEQ ID NO: 30) |
| V G W C G F E R C S S A, | (SEQ ID NO: 31) |
| L E W C G F S R C E V G, | (SEQ ID NO: 24) |
| L C Q E R L S Q R C G V, | (SEQ ID NO: 26) |
| W V L C G Q G C G G T A, | (SEQ ID NO: 27) |
| or |  |
| R C Q V Q V M V L C A L. | (SEQ ID NO: 28) |

The present disclosure also provides isolated peptides, in which the peptide contains a portion of an A domain of a v.1 or v.2 factor H binding protein (fHbp). The portion comprises an epitope for JAR 4 antibody. Isolated polypeptide may also be conjugated to additional elements at the C- and/or N-terminal end (e.g., the C-terminus and/or the N-terminus), such as a carrier molecule or a fatty acid moiety (e.g. a lauroyl residue).

The present disclosure also provides nucleic acids encoding the above described peptides and polypeptides.

The present disclosure further provides immunogenic compositions comprising a JAR 4 epitope-containing peptide of the present disclosure and a pharmaceutically acceptable excipient. In related embodiments, the immunogenic composition of claim 13, wherein the peptide is coupled to a carrier molecule (e.g., a carrier protein, e.g., a KLH protein). The peptide may also be conjugated to a fatty acid, such as a lauroyl group. In related embodiments, the immunogenic composition is provided in a formulation comprising an adjuvant. In related embodiments, the immunogenic composition is provided in a formulation comprising a polypeptide comprising an amino acid sequence of a factor H binding protein (fHbp) that is specifically bound by at least one of the monoclonal antibodies JAR 3, JAR 5, JAR 11, and JAR 13. The fHbp in the immunogenic composition may be obtained from a N. meningitidis cell that is genetically modified to express the fHbp. In addition or alternatively, the host cells may be genetically modified to contain a mutation in the LPS biosynthesis pathway (e.g. where the expression of the lpxL1 gene is attenuated).

The immunogenic composition may also contain outer membrane vesicles, membrane vesicles, or a mixture of outer membrane and membrane vesicles obtained from Neisseria cells. The vesicles may optionally be treated with a detergent. The Neisseria cells from which the vesicles are obtained may also be genetically modified as described above.

The present disclosure also provides methods of inducing an immune response to Neisseria meningitidis in subject, comprising: administering an immunogenic composition comprising a JAR 4 epitope-containing peptide of the present disclosure to a subject (e.g., a human) in an amount effective to elicit production of antibodies to the peptide in the subject.

The present disclosure also provides methods of inducing an immune response to Neisseria meningitidis in subject, comprising: administering to a subject an immunogenic composition comprising a JAR 4 epitope-containing peptide of at least 9 amino acids in length and comprising the sequence:

$DX_1X_2$ wherein $X_1$ is histidine (H) or aspartic acid (D); $X_2$ is lysine (K) or arginine (R); the aspartic acid residue (D) does not contain an N-terminal amino group; the peptide does not comprise a full-length A domain of a factor H binding protein; and the peptide is specifically bound by JAR 4 monoclonal antibody secreted by the hybridoma deposited as ATCC Accession No. PTA-8943, wherein said administering is effective to elicit production of antibodies to the peptide in the subject.

In related embodiments, $X_1$ is histidine (H) and $X_2$ is lysine (K). In further related embodiments, the peptide comprises an amino acid sequence of LEGTE (SEQ ID NO:1), TQL, AQT, TANQ (SEQ ID NO:3), or HGF immediately C-terminal to $X_2$. In related embodiments, $X_1$ is aspartic acid (D) and $X_2$ is lysine (K). In related embodiments, the peptide comprises an amino acid sequence of TGCA (SEQ ID NO:2) immediately C-terminal to $X_2$. In related embodiments, $X_1$ is histidine (H) and $X_2$ is arginine (R). In related embodiments, the peptide comprises an amino acid sequence of SGC, IWP, or HML immediately C-terminal to $X_2$.

BRIEF DESCRIPTION OF THE DRAWINGS

FIG. 1 is a schematic of an exemplary fHbp, indicating the A, B, and C domains and other structural features of the polypeptide. The amino acid sequence shown (SEQ ID NO:63) is for that of a v.1 fHbp (Neisseria.org peptide ID number 1, encoded by a gene from strain MC58).

FIG. 2 provides a table summarizing cross-reactivity of the different JAR monoclonal antibodies (mAbs), their respective Ig isotypes and ability to inhibit binding of human fH.

FIG. 5, panels B-D present a set of graphs illustrating the binding of Complement component (C4) to live encapsulated *N. meningitidis* strain NZ98/254, as determined by indirect fluorescence flow cytometry. Filled area in each panel represents 1/10 dilution of negative control antiserum from mice immunized with adjuvant alone (filled area). Panel B, JAR 4 (G2a) at 50 µg/mL. Panel C, JAR 5 (G2b) at 50 µg/mL. Panel D, combination of JAR 4 and JAR 5 at 2 µg/mL.

FIG. 7 is a schematic showing (Panel A) an amino acid sequence of a portion of a wild type v.1 fHbp A domain containing the DHK tripeptide sequence of strain MC58, as well as the corresponding amino acid sequences of the D25A, H26A and K27A mutants; (Panel B) an alignment of wild type v.1 and v.3 fHbp amino acid sequences from a portion of the A domain. In residues 1 through 60, the amino acid sequence of v.2 fHbp has one amino acid difference compared with that of v.1 fHbp.

FIG. 8 is a schematic of the sequences of JAR 4 epitope-containing peptides and the corresponding encoding nucleic acids. Lower case "q" represents an amber stop codon [TAG] in the corresponding phage library clone insert sequence, which is translated into glutamine (Q) in *E. coli* supE44 strains that are used for bacteriophage production.

Figure 3:
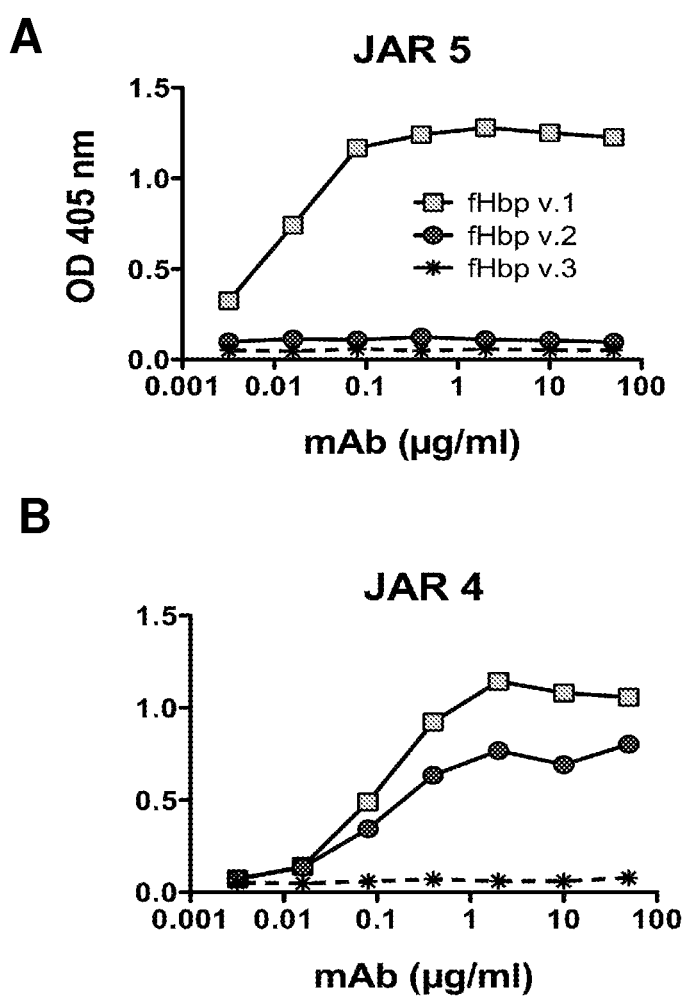
FIG. 3, panel A and panel B are graphs illustrating the specificity of JAR 5 and JAR 4 mAbs, respectively, in binding to different variants of fHbp. Binding of anti-fHbp mAbs to fHbp by a second antibody was measured by ELISA. Panel A, Binding of JAR 5 to fHbp v.1, v.2, and v.3. Panel B, Binding of JAR 4 to fHbp v.1, v.2, and v.3.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. To the extent such publications may set out definitions of a term that conflict with the explicit or implicit definition of the present disclosure, the definition of the present disclosure controls.

It must be noted that as used herein and in the appended claims, the singular forms "a", "an", and "the" include plural referents unless the context clearly dictates otherwise. Thus, for example, reference to "an antigen" includes a plurality of such antigens and reference to "the protein" includes reference to one or more proteins, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

Overview

The peptides of the present disclosure contain an epitope bound by the monoclonal antibody (mAb) JAR 4, which is produced by the hybridoma having ATCC Accession No. PTA-8943, deposited Feb. 7, 2008). JAR 4 binds an epitope of the A domain of fHbps of both v.1 and v.2, and minimally binds to the A domain of v.3 fHbp. JAR 4 does not block factor H (1H) binding and elicits no detectable bactericidal activity when tested with human complement in the absence of other anti-fHbp antibodies. However, JAR 4 facilitates cooperative complement-mediated bactericidal activity when bound to fHbp in the presence of a second mAb that binds an epitope in the B or C domain Thus antibodies to the A domain can contribute to bactericidal activity of antibodies to other portions of fHbp. Thus, peptides that present an epitope bound by JAR 4 could potentially be used to elicit anti-fHbp antibodies having the properties of JAR 4 antibodies. Such peptides find particular use in combination with fHbp-containing vaccines (e.g. fHbp vaccines that lack all or a portion of an A domain or that contain an A domain in which the JAR 4 epitope is not expressed, poorly expressed or labile), to enhance the bactericidal activity of an anti-Neisserial immune response elicited by the vaccine in a host.

The present disclosure provides peptides containing a JAR 4 epitope, and as such find use in eliciting antibodies that have the properties of JAR 4, and methods of use of such peptides in preparation of vaccines and in methods of eliciting anti-fHbp antibodies to facilitate an anti-Neisserial immune response. Exemplary embodiments of such are described below.

DEFINITIONS

"Factor H Binding Protein" (fHbp), which is also known in the literature as GNA1870, GNA 1870, ORF2086, LP2086 (lipoprotein 2086), and "741" refers to a polypeptide of *N. meningitidis* that is a lipoprotein presented on the surface of the bacterium. *N. meningitidis* strains have been sub-divided into three fHbp variant groups (referred to as variant 1 (v.1), variant 2 (v.2), and variant 3 (v.3) in some reports (Masignani et al. 2003, supra) and Family A and B in other reports (see, e.g., Fletcher et al. 2004 *Infect Immun* 2088-2100) based on amino acid sequence variability and immunologic cross-reactivity (Masignani et al. *J Exp Med* 2003; 197:789-99). For clarity, the present disclosure uses the v.1, v.2 and v.3 terminology. See FIG. 1 for numbering convention adopted herein with fHbp of MC58 as the reference. For convenience, the protein was divided into three domains, A, B, and C based on reactivity of mouse antisera prepared against the three fHbp variants with overlapping peptides spanning the entire sequence of the v.1 protein (Giuliani et al., 2005). The A domain spanned residues 8-101, the B domain spanned residues 101-164 and the C domain spanned residues 164-255. Subsequently, three-dimensional structures of the protein determined by NMR spectroscopy or X-ray crystallography identified two structural domains, termed the amino-(N-) and carboxyl-(C-)terminal domains (Mascioni et al. (2009) J. Biol. Chem. 284:8738-46; Cantini et al. (2009) J Biol. Chem. 284:9022-6; Schneider et al. (2009) Nature 458:890-3).

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

It will be appreciated that throughout this present disclosure reference is made to amino acids according to the single letter or three letter codes. For the reader's convenience, the single and three letter amino acid codes are provided below:

| G | Glycine | Gly | P | Proline | Pro |
| A | Alanine | Ala | V | Valine | Val |
| L | Leucine | Leu | I | Isoleucine | Ile |

-continued

| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The term "heterologous" refers to two components that are defined by structures derived from different sources. For example, where "heterologous" is used in the context of a polypeptide, where the polypeptide includes operably linked amino acid sequences that can be derived from different polypeptides (e.g., a first component consisting of a recombinant peptide and a second component from a native fHbp polypeptide). Similarly, "heterologous" in the context of a polynucleotide encoding a chimeric polypeptide includes operably linked nucleic acid sequence that can be derived from different genes (e.g., a first component from a nucleic acid encoding a peptide according to an embodiment disclosed herein and a second component from a nucleic acid encoding a native fHbp polypeptide). In certain embodiments, the second component may be a chimeric or a recombinant fHbp. In other cases, the second component may be a carrier molecule, e.g., a carrier protein. Such fusion polypeptides as described herein provide for presentation of epitopes in a single polypeptide that are normally found in different polypeptides. Other exemplary "heterologous" nucleic acids include expression constructs in which a nucleic acid comprising a coding sequence is operably linked to a regulatory element (e.g., a promoter) that is from a genetic origin different from that of the coding sequence (e.g., to provide for expression in a host cell of interest, which may be of different genetic origin relative to the promoter, the coding sequence or both). For example, a T7 promoter operably linked to a polynucleotide encoding an fHbp polypeptide or domain thereof is said to be a heterologous nucleic acid. "Heterologous" in the context of recombinant cells can refer to the presence of a nucleic acid (or gene product, such as a polypeptide) that is of a different genetic origin than the host cell in which it is present. For example, a Neisserial amino acid or nucleic acid sequence of one strain is heterologous to a Neisserial host of another strain.

The term "operably linked" refers to functional linkage between molecules to provide a desired function. For example, "operably linked" in the context of nucleic acids refers to a functional linkage between nucleic acids to provide a desired function such as transcription, translation, and the like, e.g., a functional linkage between a nucleic acid expression control sequence (such as a promoter, signal sequence, or array of transcription factor binding sites) and a second polynucleotide, wherein the expression control sequence affects transcription and/or translation of the second polynucleotide. "Operably linked" in the context of a polypeptide refers to a functional linkage between amino acid sequences (e.g., of different domains) to provide for a described activity of the polypeptide (e.g., presentation of an epitope to facilitate production of antibodies that specifically bind that epitope).

As used herein in the context of the structure of a peptide, "N-terminus" and "C-terminus" refer to the extreme amino and carboxyl ends of the peptide, respectively, while "N-terminal" and "C-terminal" refer to relative positions in the amino acid sequence of the peptide toward the N-terminus and the C-terminus, respectively, and can include the residues at the N-terminus and C-terminus, respectively "Immediately N-terminal" or "immediately C-terminal" refers to a position of a first amino acid residue relative to a second amino acid residue where the first and second amino acid residues are covalently bound to provide a contiguous amino acid sequence. Thus reference to an amino acid residue that is "N-terminal" to a DHK tripeptide motif present in an amino acid sequence of 9 amino acid residues in length indicates that the amino acid residue may be positioned" immediately N-terminal" or "immediately C-terminal" to the DHK sequence to provide a contiguous amino acid sequence with DHK, or may be positioned toward the N-terminus with one or more intervening residues (including being positioned at the N-terminus).

"Derived from" in the context of an amino acid sequence or polynucleotide sequence (e.g., an amino acid sequence "derived from" a v.1 fHbp) is meant to indicate that the polypeptide or nucleic acid has a sequence that is based on that of a reference polypeptide or nucleic acid (e.g., a naturally occurring fHbp protein or encoding nucleic acid), and is not meant to be limiting as to the source or method in which the protein or nucleic acid is made. "Derived from" in the context of bacterial strains is meant to indicate that a strain was obtained through passage in vivo, or in in vitro culture, of a parental strain and/or is a recombinant cell obtained by modification of a parental strain.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease. Protective immunity can be accompanied by production of bactericidal antibodies. It should be noted that production of bactericidal antibodies against *Neisseria meningitidis* is accepted in the field as predictive of a vaccine's protective effect in humans (Goldschneider et al., 1969, *J. Exp. Med.* 129:1307; Borrow et al. 2001 *Infect Immun.* 69:1568).

The phrase "a disease caused by *Neisseria meningitidis*" encompasses any clinical symptom or combination of clinical symptoms that are present in an infection of a human with *Neisseria meningitidis*. These symptoms include but are not limited to: colonization of the upper respiratory tract (e.g. mucosa of the nasopharynx and tonsils) by a pathogenic strain of *Neisseria meningitidis*, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischaemia, respiratory distress syndrome, pericarditis and meningitis.

The phrase "broad spectrum protective immunity" means that a vaccine or immunization schedule elicits "protective immunity" against at least more than one strain (and can be against at least two, at least three, at least four, at least five, against at least eight, or more strains) of *Neisseria meningitidis*, wherein each of the strains expresses a different fHbp subvariant or fHbp variant. The present disclosure specifically contemplates and encompasses a vaccine and vaccination regimen that confers protection against a disease caused by a member of any capsular group (e.g., A, B, or C), with protection against disease caused by a capsular group B strain of *Neisseria meningitidis* being of interest due to the epidemiological prevalence of strains causing disease with this capsular group and lack of broadly effective group B vaccines. For example, the peptides of the present disclosure alone or in combination with fHbp of a fragment thereof that presents an epitope(s) of interest can be used to elicit antibody responses that cross-react across capsular groups where the major fHbp antigenic groups are included (e.g., v.1 and v.2).

The terms "host" or "subject" are used interchangeably herein to refer to a human and non-human animal, where non-human animals are generally referred to in the context of production of anti-*N. meningitidis* antibodies and humans are hosts of interest for vaccination to reduce the risk of disease by *N. meningitidis* infection.

The phrase "specifically binds to an antibody" or "specifically immunoreactive with", in the context of an antigen (e.g., a polypeptide antigen) refers to a binding reaction which is based on and/or is probative of the presence of the antigen in a sample which may also include a heterogeneous population of other molecules. Thus, under designated conditions, the specified antibody or antibodies bind(s) to a particular antigen or antigens in a sample and do not bind in a significant amount to other molecules present in the sample. "Specifically binds to an antibody" or "specifically immunoreactive with" in the context of an epitope of an antigen (e.g., an epitope of a polypeptide) refers to a binding reaction which is based on and/or is probative of the presence of the epitope in an antigen (e.g., polypeptide) which may also include a heterogeneous population of other epitopes, as well as a heterogeneous population of antigens. Thus, under designated conditions, the specified antibody or antibodies bind(s) to a particular epitope of an antigen and does not bind in a significant amount to other epitopes present in the antigen and/or in the sample.

The phrase "in a sufficient amount to elicit an immune response" means that there is a detectable difference between an immune response indicator measured before and after administration of a particular antigen preparation. Immune response indicators include but are not limited to: antibody titer or specificity, as detected by an assay such as enzyme-linked immunosorbent assay (ELISA), bactericidal assay, flow cytometry, immunoprecipitation, Ouchterlony immunodiffusion; binding detection assays of, for example, spot, Western blot or antigen arrays; cytotoxicity assays, etc.

A "surface antigen" is an antigen that is present in a surface structure of a cell, particularly a bacterium such as *Neisseria meningitidis* (e.g. the outer membrane, inner membrane, periplasmic space, capsule, pili, etc.).

"Isolated" refers to a compound of interest that, if naturally occurring, is in an environment different from that in which it may naturally occur. "Isolated" is meant to include compounds that are within samples that are substantially enriched for the compound of interest and/or in which the compound of interest is partially or substantially purified. Where the compound is not naturally occurring, "isolated" indicates the compound has been separated from an environment in which it was made by either synthetic or recombinant means.

"Enriched" means that a sample is non-naturally manipulated (e.g., by an experimentalist or a clinician) so that a compound of interest is present in a greater concentration (e.g., at least a three-fold greater, at least 4-fold greater, at least 8-fold greater, at least 64-fold greater, or more) than the concentration of the compound in the starting sample, such as a biological sample (e.g., a sample in which the compound naturally occurs or in which it is present after administration), or in which the compound was made (e.g., as in a bacterial polypeptide, antibody, chimeric polypeptide, and the like).

"Substantially pure" indicates that an entity (e.g., polypeptide) makes up greater than about 50% of the total content of the composition (e.g., total protein of the composition) and typically, greater than about 60% of the total protein content. More typically, a "substantially pure" refers to compositions in which at least 75%, at least 85%, at least 90% or more of the total composition is the entity of interest (e.g., of the total protein. Preferably, the protein will make up greater than about 90%, and more preferably, greater than about 95% of the total protein in the composition.

JAR 4 mAb-Binding Peptides

The present JAR 4 epitope-containing peptides which find use in eliciting antibodies that bind an epitope on fHbp bound by the JAR 4 mAb. Such JAR 4 epitope-containing peptides find use in production of immunogenic compositions which can be used in methods of eliciting anti-fHbp antibodies to facilitate an anti-Neisserial immune response.

In general JAR 4 epitope-containing peptides are at least 9 amino acid residues in length, and usually are at least 9 to 30 amino acid residues in length, at least 9 to 25 amino acid residues in length, at least 9 to 20 amino acid residues in length, at least 12 to 30 amino acid residues in length, at least 12 to 20 amino acid residues in length, or at least 12 to 25 amino acid residues in length.

In one embodiment, the JAR 4 epitope-containing peptides are at least 9 amino acids in length and comprises the tripeptide sequence:

$DX_1X_2$ wherein
$X_1$ is histidine (H) or aspartic acid (D);
$X_2$ is lysine (K) or arginine (R),
the aspartic acid residue (D) does not contain an N-terminal amino group (e.g., is modified so as to be covalently bound to a moiety through the terminal amino group, e.g., such that at least one amino acid residue N-terminal to the motif, e.g., H, F, Y or K);
the peptide contains at least 3 amino acid residues immediately C-terminal to $X_2$, wherein the at least 3 amino acid residues may optionally comprise:

LEG,

QLD,

AQT,

SGC,

TAN,

IWP,

HML,
or

HGF, the polypeptide does not comprise a full-length A domain of a fHbp; and the peptide is specifically bound by a JAR 4 mAb.

Exemplary JAR 4 epitope-containing peptides include those wherein $X_1$ is histidine (H) and $X_2$ is lysine (K) (i.e., contain a DHK tripeptide motif); wherein $X_1$ is aspartic acid (D) and $X_2$ is lysine (K) (i.e., contain a DDK tripeptide motif); and wherein $X_1$ is histidine (H) and $X_2$ is arginine (R) (i.e., contain a DHR tripeptide motif).

Further exemplary JAR 4 epitope-containing peptides including those having a DHK tripeptide motif, and comprising immediately C-terminal to DHK comprise an amino acid sequence of LEGTE (SEQ ID NO:1), TQL, AQT, TANQ (SEQ ID NO:3), or HGF.

Exemplary JAR 4 epitope-containing peptides also include those having a DDK tripeptide motif, and comprising immediately C-terminal to DHK an amino acid sequence of TGCA (SEQ ID NO:2).

Exemplary JAR 4 epitope-containing peptides further include those having a DHR tripeptide motif, and comprising immediately C-terminal to DHK an amino acid sequence of SGC, IWP, or HML.

Exemplary $DX_1X_2$ tripeptide-containing peptides include those at least 9 amino acid residues in length, and, in addition to the $DHX_1$ formula as described above, comprises at least 7 contiguous amino acids of an amino acid sequence of a peptide in the table below:

|  | SEQ ID NO: |
|---|---|
| H D H K L E G T E | 14 |
| C G G V Y D D K T G C A | 15 |
| H D H K T Q L D P | 16 |
| W T L A V F D H K A Q T | 17 |
| G C M G Y D H R S G C V | 18 |
| F H D H K T A N Q | 19 |
| H D H R I W P L D V T A | 21 |
| K D H R H M L W P E E S | 25 |
| H D H K F G F Q E P A S | 29 | wherein
the peptide contains DHK, DDK, or DHR,
the aspartic acid (D) of DHK, DDK, or DHR does not contain an N-terminal amino group when present at the peptide N-terminal end; and
the peptide is specifically bound by JAR 4 mAb.

JAR 4 epitope-containing peptides can also be derived from a portion of an amino acid sequence of an A domain of a v.1 or v.2 fHbp. In such embodiments, the peptide can be 9 to 99, 9 to 90, 9 to 80, 9 to 60, 9 to 40, 9 to 20, or 9 to 12 contiguous amino acids of an A domain of v.1 or v.2 fHbp, with the proviso that the peptide contains the DHK tripeptide sequence or a variant thereof that retains JAR 4 binding. Exemplary peptides include those comprising the contiguous amino acid sequence:

L D H K D K G          (SEQ ID NO: 4)

Other exemplary JAR 4 epitope-containing peptides include those at least 9 amino acid residues in length and comprises a contiguous amino acid sequence of at least 5, 6, 7, 8, 9, 10, 11, or 12 residues of a peptide exemplified in the table below:

|   |   |   |   |   |   |   |   |   |   | SEQ ID NO: |
|---|---|---|---|---|---|---|---|---|---|---|
| N | D | E | R | Q | M | S | D | W | Y | R | A | 22 |
| H | V | H | R | G | S | Q | G | G | Q | R | Q | 23 |

Other exemplary JAR 4 epitope-containing peptides include those at least 9 amino acid residues in length and comprises the contiguous amino acid sequence WCGF (SEQ ID NO:71). Further exemplary JAR 4 epitope-containing peptides include those at least 9 amino acid residues in length and comprises the contiguous amino acid sequence WCG-FER (SEQ ID NO:72). In other embodiments, the JAR 4 epitope-containing peptide comprises a contiguous amino acid sequence of at least 5, 6, 7, 8, 9, 10, 11, or 12 residues of a peptide exemplified in the table below:

|   |   |   |   |   |   |   |   |   |   | SEQ ID NO: |
|---|---|---|---|---|---|---|---|---|---|---|
| W | R | <u>W</u> | <u>C</u> | <u>G</u> | F | E | R | C | P | E | G | 20 |
| S | D | W | <u>G</u> | <u>W</u> | G | <u>G</u> | R | A | E | Q | H | 30 |
| V | <u>G</u> | <u>W</u> | C | <u>G</u> | F | E | R | C | S | S | A | 31 |
| L | E | W | C | G | F | S | R | C | E | V | G | 24 |
| L | C | Q | E | R | L | S | Q | R | C | G | V | 26 |
| W | V | L | C | G | Q | G | C | G | G | T | A | 27 |
| R | C | Q | V | Q | V | M | V | L | C | A | L | 28 |

The JAR 4 epitope-containing peptides disclosed herein include those of the specific contiguous amino acid sequences provided herein, as well as those having 1, 2, 3, or 4, usually no more than 4, 3, or 2, amino acid substitutions, where the substitution is usually a conservative amino acid substitution. By "conservative amino acid substitution" generally refers to substitution of amino acid residues within the following groups:

1) L, I, M, V, F;

2) R, K;

3) F, Y, H, W, R;

4) G, A, T, S;

5) Q, N;
and

6) D, E.

Conservative amino acid substitutions in the context of a peptide or polypeptide disclosed herein are selected so as to preserve presentation of an epitope of interest. Such presentation may be preserved by substituting with an amino acid with a side chain of similar acidity, basicity, charge, polarity, or size to the side chain of the amino acid being replaced. Guidance for such substitutions may also be based on alignments of amino acid sequences of polypeptides presenting the epitope of interest.

JAR 4 epitope-containing peptides can be provided as fusion proteins containing 1, 2, 3, or 4 or more JAR 4 epitope-containing peptides as described herein. JAR 4 epitope-containing peptides can also be provided as fusion proteins with a polypeptide(s) derived from an fHbp polypeptide. For example, the JAR 4 epitope-containing peptide can be fused to an N-terminal end of a naturally occurring or chimeric fHbp having at least B and C domains. JAR 4 epitope-containing peptides can be inserted into an fHbp so as to substitute the amino acid sequence of a JAR 4 epitope-containing peptide with the native DHK-containing sequence of the fHbp.

In addition to the above, the peptides of the present disclosure may also contain one or more additional elements at the N- and/or C-terminus of the peptide, such as a polypeptide (e.g. having an amino acid sequence heterologous to the subject peptide) and/or a carrier molecule. Exemplary elements that may be linked to the subject peptide include a fatty acid moiety (e.g. an aliphatic carboxylic acid) and/or a carrier molecule (e.g., a carrier protein, e.g. KLH). Such additional elements may be linked to the peptide via a linker, e.g. a flexible linker. For example, the peptide may be conjugated to a carrier molecule, e.g., to facilitate administration and/or to increase the immunogenicity in a subject to be vaccinated or treated against *N. meningitidis*. Carrier molecules can also facilitate delivery to a cell or tissue of interest. The additional moiety may also aid in immunogenicity or forming a complex with a component in a vaccine. The carrier molecules of such modified peptides may act as a scaffold protein to facilitate display of the peptide on a membrane surface (e.g. a vesicle vaccine).

In one embodiment of interest, JAR 4 epitope-containing peptides are modified at the N- and/or C-terminus to include a fatty acid (e.g. aliphatic carboxylic acid group). The fatty acid may be covalently linked to the peptide via a flexible linker.

An exemplary fatty acid that may be used to modify an end (e.g. N-terminal end, e.g., at the N-terminus) of the subject peptides is lauric acid. Lauric acid when covalently attached to another molecule is referred to as an lauroyl group (e.g. lauroyl sulfate). Lauric acid contains twelve carbon atoms with ten methylene groups and the formula $CH_3—(CH_2)_{10}—COOH$. Other fatty acids that may be linked to the subject peptides include caprylic acid (10 C), myristic acid (14 C), and palmitic acid (16 C). For details, see Westerink M A et al. (1995) *Proc. Natl. Acad. Sci. USA* 92:4021-4025. It is also contemplated that any hydrophobic moiety that can serve to anchor the subject peptide into the bacterial outer membrane is contemplated herein for conjugation to a N- and/or C-terminal end (e.g., at the N-temrinus) of the peptides of the present disclosure, where the hydrophobic moiety can be optionally conjugated to the peptide through a linker, e.g., a flexible linker, as described herein. For example, a hydrophobic pentapeptide FLLAV (SEQ ID NO: 5), as described in Lowell G H et al. (1988) *J. Exp. Med.* 167:658-63.

One way in which the fatty acid, as well as other additional elements execmplified above, is connected to the peptide is via a linker (e.g. lauroyl-Gly-Gly). Linkers suitable for use in modifying the peptides of the present disclosure include "flexible linkers". Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO: 6) and $GGGS_n$ (SEQ ID NO: 7), where n is an integer of at least one), glycine-alanine polymers, alanine-serine polymers, and other flexible linkers known in the art. Glycine and glycine-serine polymers are of interest since both of these amino acids are relatively unstructured, and therefore may may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited GGSG (SEQ ID NO: 8), GGSGG (SEQ ID NO: 9), GSGSG (SEQ ID NO: 10), GSGGG (SEQ ID NO: 11), GGGSG (SEQ ID NO: 12), GSSSG (SEQ ID NO: 13), and the like. The ordinarily skilled artisan will recognize that design of a peptide conjugated to any elements described above can include linkers that are all or partially flexible, such that the linker can include a flexible linker as well as one or more portions that confer less flexible structure.

Methods of Production

The JAR 4 epitope-containing peptides can be produced by any suitable method, including recombinant and non-recombinant methods (e.g., chemical synthesis). Where the peptide is chemically synthesized, the synthesis may proceed via a liquid-phase or solid-phase. Solid-phase synthesis (SPPS) allows the incorporation of unnatural amino acids, peptide/protein backbone modification. Various forms of SPPS, such as Fmoc and Boc, are available for synthesizing peptides of the present invention. Details of the chemical synthesis are known in the art (e.g. Ganesan A., Mini Rev. Med. Chem. (2006) 6:3-10. and Camarero J A et al., Protein Pept Lett. (2005) 12:723-8).

Briefly, small insoluble, porous beads are treated with functional units on which peptide chains are built. After repeated cycling of coupling/deprotection, the free N-terminal amine of a solid-phase attached is coupled to a single N-protected amino acid unit. This unit is then deprotected, revealing a new N-terminal amine to which a further amino acid may be attached. The peptide remains immobilized on the solid-phase and undergoes a filtration process before being cleaved off.

Where the JAR 4 epitope-containing peptide is produced using recombinant techniques, the methods can involve any suitable construct and any suitable host cell, which can be a prokaryotic or eukaryotic cell, usually a bacterial or yeast host cell, more usually a bacterial cell.

Bacterial cells, such as *Neisseria* bacteria, may be used to produce JAR 4 epitope-containing peptide, e.g. where the peptide is to be provided in a vesicle-based vaccine. Any of a variety of *Neisseria* strains that produce or be modified to produce fHbp, and, optionally, other antigens of interest, such as PorA, GNA2132 etc., can be used in the methods to produce the peptides of the present disclosure. Pathogenic *Neisseria* spp. or strains derived from pathogenic *Neisseria* spp., particularly strains pathogenic for humans or derived from strains pathogenic or commensal for humans, are of particular interest. Exemplary *Neisserial* spp. include *N. meningitidis, N. flavescens N. gonorrhoeae, N. lactamica, N. polysaccharea, N. cinerea, N. mucosa, N. subflava, N. sicca, N. elongata,* and the like. "Derived from" in the context of bacterial strains is meant to indicate that a strain was obtained through passage in vivo, or in in vitro culture, of a parental strain and/or is a recombinant cell obtained by modification of a parental strain.

Exemplary *N. meningitidis* strains that may be used as host cells can be of any serologic group, serotype or subtype, e.g. serogroups A, B, C, X, Y, Z, 29-E, and W-135. Strains of the serogroups A, B, C, Y and W-135 are of particular interest.

The particular type of host cells that is used to express the recombinant peptide may also be the same *N. meningitidis* strain that expresses the membrane vesicles to be included in a combination antigenic composition, which is described in more detail below. For example, the strain used to produce the outer membrane vesicles (OMV) may be the same strain the expresses one or more recombinant JAR 4-epitope containing peptides of the present disclosure.

The host cells used in the subject method may also express an endogenous or exogenous fHbp. Where the host cell is a *N. meningitidis* strain the host cell may have a knock-out of the endogenous fHbp gene and be genetically modified to express an exogenous fHbp (e.g. encoded by a transfected vector or other genetic element that allows for expression of the protein inside the host cell). The exogenous fHbp that is expressed by the host cells may be derived from the same variant and/or strain as the host cells or heterologous to the variant and/or strain of the host cells. In an embodiment where the host cell expresses more than one type of fHbp, each fHbp may be derived from a different variant and/or strain. For example, a host cell may express both a variant 1 fHbp and a variant 2 fHbp.

The *N. meningitidis* may be genetically modified to have a defect in the LPS biosynthesis, as described below. For example, the host cell may be genetically modified to provide for decreased or no activity of the product of the lpxL1 gene and that produces a level of fHbp protein sufficient to provide for vesicles that, when administered to a subject, evoke serum anti-fHbp antibodies. Details on the membrane vesicle preparation and decreasing the expression of the lpxL1 gene are described later below and may also be found in US Pat. Pub. No. 20090035328 and PCT Pub. WO 2006/081259, disclosures of which are incorporated herein by reference.

Methods for introduction of genetic material into host cells include, for example, transformation, electroporation, conjugation, calcium phosphate methods and the like. The method for transfer can be selected so as to provide for stable expression of the introduced JAR 4 epitope-containing peptide-encoding nucleic acid. The polypeptide-encoding nucleic acid can be provided as an inheritable episomal element (e.g., plasmid) or can be genomically integrated. A variety of appropriate vectors for use in production of a polypeptide of interest are available commercially.

Vectors can provide for extrachromosomal maintenance in a host cell or can provide for integration into the host cell genome. The expression vector provides transcriptional and translational regulatory sequences, and may provide for inducible or constitutive expression, where the coding region is operably linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression constructs generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selectable genes are well known in the art and will vary with the host cell used.

It should be noted that polypeptide of the present disclosure may comprise additional elements, such as a detectable label, e.g., a radioactive label, a fluorescent label, a biotin label, an immunologically detectable label (e.g., an HA tag, a poly-Histidine tag) and the like. Additional elements can be provided to facilitate isolation (e.g., biotin tag, immunologically detectable tag) through various methods (e.g., affinity capture, etc.). The polypeptide can optionally be immobilized on a support through covalent or non-covalent attachment.

JAR 4 epitope-containing peptides can be bound to a carrier protein so as to facilitate presentation of the JAR 4 epitope to the immune system. Exemplary carrier proteins include serum albumin (e.g. bovine serum albumin (BSA)), ovalbumin, keyhole limpet hemacyanin (KLH), bovine thyroglobulin, soybean trypsin inhibitor or purified protein derivative of tuberculin (PPD). In some embodiments, peptide immunogens are provided as a fusion protein composed of a JAR 4 epitope-containing peptide flanked on one or both termini by a heterologous polypeptide, e.g., a region of a pVIII phage protein Coupling may be achieved using a bifunctional coupling agent, such as maleimidobenzoyl sulfosuccinimide ester (conjugation through cysteine residues), N-hydroxysuccinimide (through lysine residues), carbodiimide, glutaraldehyde, succinic anhydride, and the like. Alternatively, or in addition, the antigen and carrier protein may be generated as a fusion protein.

In one embodiment, the JAR 4 epitope-containing peptides are provided as a fusion protein in a carrier protein to facilitate presentation of the JAR 4 epitope to the immune system and thus facilitate production of anti-*N. meningitidis* antibodies having properties of JAR 4 mAb. A JAR 4 epitope-containing peptide can be fused at the N-terminus, fused at the C-terminus, or positioned in the scaffold such that the amino acid sequence of the JAR 4 epitope-containing peptide is flanked by carrier protein sequence. The JAR 4 epitope-containing peptides are heterologous to the carrier protein and thus provide for a chimeric polypeptide not found in nature.

Isolation and purification of a polypeptide can be accomplished according to methods known in the art. For example, a polypeptide can be isolated from a lysate of cells genetically modified to express the polypeptide, or from a synthetic reaction mixture, by immunoaffinity purification, which generally involves contacting the sample with an anti-JAR 4 epitope-containing peptide antibody (e.g., JAR 4 mAb), washing to remove non-specifically bound material, and eluting the specifically bound polypeptide. The isolated polypeptide can be further purified by dialysis and other methods normally employed in protein purification methods. In one embodiment, the polypeptide may be isolated using metal chelate chromatography methods.

The JAR 4 epitope-containing peptides may be prepared in substantially pure or isolated form (e.g., free from other polypeptides). In certain embodiments, the polypeptide is present in a composition that is enriched for the polypeptide relative to other components that may be present (e.g., other polypeptides or other host cell components). Purified polypeptide may be provided such that the polypeptide is present in a composition that is substantially free of other expressed polypeptides, e.g., less than 90%, usually less than 60% and more usually less than 50% of the composition is made up of other expressed polypeptides.

Nucleic Acids

As discussed above, the subject polypeptide may be generated using recombinant techniques to manipulate nucleic acids of different fHbps known in the art to provide constructs encoding a polypeptide of interest. It will be appreciated that provided an amino acid sequence, the ordinarily skilled artisan will immediately recognize a variety of different nucleic acids encoding such amino acid sequence in view of the knowledge of the genetic code.

For production of JAR 4 epitope-containing peptides derived from naturally-occurring polypeptides, it is noted that nucleic acids encoding a variety of different v.1, v.2, and v.3 fHbps of *N. meningitidis* are known and available in the art. Exemplary fHbp polypeptides and their nucleic acids are described in, for example, WO 2004/048404; Masignani et al. 2003 J Exp Med 197:789-799; Fletcher et al. Infect Immun 2004 2088-2100; Welsch et al. J Immunol 2004 172:5606-5615; and WO 99/57280. Nucleic acid (and amino acid sequences) for fHbp variants and subvariants are also provided in GenBank as accession nos.: NC_003112, GeneID: 904318 (NCBI Ref. NP_274866) (from *N. meningitidis* strain MC58); AY548371 (AAT01290.1) (from *N. meningitidis* strain CU385); AY548370 (AAT01289.1) (from *N. meningitidis* strain H44/76); AY548377 (AAS56920.1) (from *N. meningitidis* strain M4105); AY548376 (AAS56919.1) (from *N. meningitidis* strain M1390); AY548375 (AAS56918.1) (from *N. meningitidis* strain N98/254); AY548374 (AAS56917.1) (from *N. meningitidis* strain M6190); AY548373 (AAS56916.1) (from *N. meningitidis* strain 4243); and AY548372 (AAS56915.1) (from *N. meningitidis* strain BZ83). While *N. meningitidis* strains of any capsular group may be used, *N. meningitidis* strains of capsular group B are of particular interest as sources from which nucleic acid encoding fHbp and domains thereof are derived.

It will be appreciated that the nucleotide sequences encoding the subject polypeptide may be modified so as to optimize the codon usage to facilitate expression in a host cell of interest (e.g., *E. coli, N. meningitidis*, human (as in the case of a DNA-based vaccine), and the like). Methods for production of codon optimized sequences are known in the art.

Formulations

"Antigen composition", "antigenic composition" or "immunogenic composition" is used herein as a matter of convenience to refer generically to compositions comprising a JAR 4 epitope-containing peptide as disclosed herein, which the subject polypeptide may be optionally conjugated and/or provided in combination to enhance immunogenicity. Compositions useful for eliciting anti-*N. meningitidis* antibodies, particularly antibodies against *Neisseria meningitidis* group B (NmB), in a human are specifically contemplated by the present disclosure. Antigenic compositions can contain 2, 3, 4, 5, 6 or more different JAR 4 epitope-containing peptides as described herein, where each subject peptide may differ in amino acid sequence. Optionally, the peptide can combined with polypeptides from different fHbp variants and/or subvariants (e.g., either in admixture or as part of a fusion protein).

Antigenic compositions generally comprise an immunologically effective amount of a JAR 4 epitope-containing peptide, and may further include other compatible components, as may be desired. By "immunologically effective amount" is meant that the administration of that amount to an individual, either in a single dose, as part of a series of the same or different antigenic compositions, is effective to elicit an antibody response effective for treatment or prevention of a symptom of, or disease caused by, for example, infection by *Neisseria*, particularly *N. meningitidis*, more particularly Group B *N. meningitidis*. This amount varies depending upon the health and physical condition of the individual to be treated, age, the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials.

The concentration of the JAR 4 epitope-containing peptide in a formulation can vary widely (e.g., from less than about 0.1%, usually at or at least about 2% to as much as 20% to 50% or more by weight) and will usually be selected primarily based on fluid volumes, viscosities, and patient-based factors in accordance with the particular mode of administration selected and the patient's needs.

The compositions can include additional antigens, e.g., polypeptide antigens that can elicit anti-fHbp antibodies in addition to or other than JAR 4. For example, the JAR 4 epitope-containing peptides can be provided in combination with polypeptides comprising amino acid sequences of a v.1, v.2, and/or v.3 fHbp, e.g., to provide for production of antibodies that bind epitopes of the mAbs JAR 3, of JAR 5, JAR 11, JAR 13, and the like. Such polypeptides include chimeric fHbp polypeptides, which contain portions or one or more of a v.1, v.2, and/or v.3 fHbp.

In one embodiment, the JAR 4 epitope-containing peptides are administered in combination with (i.e., in the same or different formulations) with a composition including one or more of the Neisserial antigens fHbp, GNA2132, NadA, GNA2091 and GNA1030, or an antigenic fragment or fusion protein thereof. Exemplary combinations include fHbp, GNA2132 and NadA; and fHbp, GNA2132, Nad A, GNA2091 and GNA1030. In one embodiment, the JAR 4 epitope-containing peptide is provided in combination with the 5 component recombinant protein vaccine as described in Giuliani et al. (Proc Natl Acad Sci USA 2006; 103:10834-9).

The JAR 4 epitope-containing peptides can be provided in combination with any of a variety of compositions containing *N. meningitidis* vesicles (e.g., microvesicles and/or outer membrane vesicles), which are produced from an *N. meningitidis* strain expressing fHbp, particularly a v.1 and/or v.2 fHbp and/or v.3 fHbp. A variety of such vesicle compositions are known in the art, and their methods of preparation from a variety of different strains well known.

Peptide compositions can be provided in a pharmaceutically acceptable excipient, which can be a solution such as a sterile aqueous solution, often a saline solution, or they can be provided in powder form. Such excipients can be substantially inert, if desired.

The peptide compositions can include an adjuvant. Examples of known suitable adjuvants that can be used in humans include, but are not necessarily limited to, alum, aluminum phosphate, aluminum hydroxide, MF59 (4.3% w/v squalene, 0.5% w/v TWEEN80™, 0.5% w/v SPAN 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as norMDP), N-acetylmuramyl-L-alanyl-D-isoglutaminyl-L-alanine-2-(1'-2'-dip-almitoyl-snglycero-3-hydroxyphos-phoryloxy)-ethylamine (CGP 19835A, referred to as MTP-PE), and RIBI, which contains three components extracted from bacteria, monophosphoryllipid A, trehalose dimycolate and cell wall skeleton (MPL+TDM+CWS) in a 2% squalene/TWEEN 80 emulsion. The effectiveness of an adjuvant may be determined by measuring the amount of antibodies directed against the immunogenic antigen or antigenic epitope thereof.

Further exemplary adjuvants to enhance effectiveness of the composition include, but are not limited to: (1) oil-in-water emulsion formulations (with or without other specific immuno stimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% TWEEN 80, and 0.5% SPAN 85 (optionally containing MTP-PE) formulated into submicron particles using a microfluidizer, (b) SAF, containing 10% Squalane, 0.4% TWEEN 80, 5% PLURONIC-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% TWEEN 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryllipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg Vaccine 2000, 19, 618-622; Krieg Curr opin Mol Ther 2001 3:15-24; Roman et al., Nat. Med, 1997, 3, 849-854; Weiner et al., PNAS USA, 1997, 94, 10833-10837; Davis et al, J. Immunol, 1998, 160, 810-876; Chu et al., J. Exp. Med, 1997, 186, 1623-1631; Lipford et al, Ear. J. Immunol., 1997,27, 2340-2344; Moldoveami e/ al., Vaccine, 1988, 16, 1216-1224, Krieg et al., Nature, 1995, 374, 546-549; Klinman et al., PNAS USA, 1996, 93, 2879-2883; Ballas et al, J. Immunol, 1996, 157, 1840-1845; Cowdery et al, J. Immunol, 1996, 156, 4570-4575; Halpern et al, Cell Immunol, 1996, 167, 72-78; Yamamoto et al, Jpn. J. Cancer Res., 1988, 79, 866-873; Stacey et al, J. Immunol., 1996, 157, 2116-2122; Messina et al, J. Immunol, 1991, 147, 1759-1764; Yi et al, J. Immunol, 1996, 157, 4918-4925; Yi et al, J. Immunol, 1996, 157, 5394-5402; Yi et al, J. Immunol, 1998, 160, 4755-4761; and Yi et al, J. Immunol, 1998, 160, 5898-5906; International patent applications WO 96/02555, WO 98/16247, WO 98/18810, WO 98/40100, WO 98/55495, WO 98/37919 and WO 98/52581, i.e. containing at least one CG dinucleotide, where the cytosine is unmethylated; (8) a polyoxyethylene ether or a polyoxyethylene ester e.g WO 99/52549; (9) a polyoxyethylene sorbitan ester surfactant in combination with an octoxynol (WO 01121207) or a polyoxyethylene alkyl ether or ester surfactant in combination with at least one additional non-ionic surfactant such as an octoxynol (WO 01121152); (10) a saponin and an immunostimulatory oligonucleotide (e.g. a CpG oligonucleotide) (WO 00/62800); (11) an immunostimulant and a particle of metal salt e.g WO 00/23105; (12) a saponin and an oil-inwater emulsion e.g. WO 99/11241; (13) a saponin (e.g QS21)+3dMPL+IM2 (optionally+a sterol) e.g WO 98/57659; (14) other substances that act as immunostimulating agents to enhance the efficacy of the composition. Muramyl peptides include N-acetyl-muramyl-Lthreonyl-D-isoglutamine (thr-MDP), N-25 acetyl-normuramyl-L-alanyl-D-isoglutamine (norMDP), N-acetylmuramyl-L-alanyl-D-isoglutarninyl-L-alanine-2-(1'-2'-dipalmitoyl-snglycero-3-hydroxyphosphoryloxy)-ethylamine MTP-PE), etc. Adjuvants suitable for administration to a human are of particular interest.

The peptide compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The peptide-containing formulations can be provided in the form of a solution, suspension, tablet, pill, capsule, powder, gel, cream, lotion, ointment, aerosol or the like. It is recognized that oral administration can require protection of the compositions from digestion. This can be accomplished either by association of the composition with an agent that renders it resistant to acidic and enzymatic hydrolysis or by packaging the composition in an appropriately resistant carrier molecule. Means of protecting from digestion are well known in the art.

The peptide-containing formulations may be provided so as to enhance serum half-life of the subject polypeptide following administration. For example, where isolated polypeptides are formulated for injection, the polypeptide may be provided in a liposome formulation, prepared as a colloid, or other conventional techniques for extending serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms.

Combination Vaccines

As noted above, the JAR 4 epitope-containing peptides can be provided in combination with any of a variety of antigenic compositions for use in eliciting an immune response against *N. meningitidis* in a subject. "Combination" as used herein is meant to include compositions that are formulated separately for separate administration (e.g., as may be provided in a kit), as well as for administration in a single formulation (i.e., "co-formulated").

For example, the antigenic compositions disclosed herein can include vesicles prepared from Neisserial cells that express the subject peptide, as described above. As referred herein, "vesicles" is meant to encompass outer membrane vesicles (OMVs) as well as microvesicles (MVs, also referred to as blebs). Vesicles can be prepared from the outer membrane of a cultured strain of *Neisseria meningitidis* that naturally produces, or is genetically modified to produce, an fHbp of interest. For example, vesicles may be obtained from *N. meningitidis* bacteria that overexpress an fHbp. The fHbp may be the same variant as the bacteria or a variant that is heterologous to the bacteria. Such *N. meningitidis* bacteria may optionally be genetically modified to provide for a knock-out of the endogenous fHbp and/or a defect in the LPS biosynthesis (e.g. due to a defect in lpxL1 expression). In some embodiments, the *N. meningitidis* strain is modified to express a chimeric fHbp. Exemplary chimeric fHbps include those described in the PCT Application No. PCT/US09/36577, disclosure of which is incorporated herein by reference. The chimeric fHbp may also be provided in the antigenic composition of the present disclosure. OMVs and MVs may be obtained from any of these *N. meningitidis* bacteria using any suitable method available in the art (see, e.g., US 2006/0029621; US 2009/0035328; WO 01/34642; and WO 2006/081259).

The antigenic compositions of the present disclosure can comprise vesicles from one strain, or from 2, 3, 4, 5 or more strains, which strains may be homologous or heterologous, usually heterologous, to one another with respect to one or more of, for example, fHbp variant group, PorA type, and the like. In one embodiment, the vesicles can be prepared from strains that express more than one embodiment of the subject polypeptide (e.g., 1, 2, 3, or more polypeptides), which may be composed of or fused to fHbp amino acid sequences from different variants (v.1, v.2, or v.3) or subvariants (e.g., a subvariant of v.1, v.2, or v.3).

The antigenic compositions can comprise a mixture of OMVs and MVs presenting the same or different polypeptides, where the polypeptides may optionally be combined or fused to epitopes from different combinations of fHbp variants and/or subvariants and where the OMVs and/or MVs may be from the same or different strains. Vesicles from different strains can be administered as a mixture, or can be administered serially. In certain embodiments, a vesicle vaccine may comprise a polypeptide according to the present invention and a recombinant or naturally-occurring fHbp. Where the host cells express a peptide of the present disclosure and also an fHbp of the desired immunogenicity, preparation of the antigenic composition may involve purifying both the polypeptide of the present disclosure and an fHbp from the same host cells.

Where the antigenic compositions contain membrane vesicles complexed with one or more peptides of the present disclosure, the peptide may be modified at one of the terminus with a fatty acid or a hydrophobic moiety, which is optionally conjugated to the peptide via a linker, as described above. The fatty acid or hydrophobic moiety may aid in the complex formation between the membrane vesicles and the JAR 4 epitope-containing peptide. For example, a peptide containing lauroyl-GG at the N-terminus may be used to prepare a vaccine composition where the peptide is complexed with a vesicle.

Where desired (e.g., where the strains used to produce vesicles are associated with endotoxin or particular high levels of endotoxin), the vesicles are optionally treated to reduce endotoxin, e.g., to reduce toxicity following administration. Although less desirable a discussed below, reduction of endotoxin can be accomplished by extraction with a suitable detergent (for example, BRIJ-96, sodium deoxycholate, sodium lauroylsarcosinate, Empigen BB, TRITON X-100, TWEEN 20 (sorbitan monolaurate polyoxyethylene), TWEEN 80, at a concentration of 0.1-10%, preferably 0.5-2%, and SDS). Where detergent extraction is used, it is preferable to use a detergent other than deoxycholate.

In some embodiments the vesicles of the antigenic compositions are prepared without detergent, e.g., without use of deoxycholate. Although detergent treatment is useful to remove endotoxin activity, it may deplete the native fHbp lipoprotein and/or chimeric fHbp (including lipidated chimeric fHbp) by extraction during vesicle production. Thus it may be particularly desirable to decrease endotoxin activity using technology that does not require a detergent. In one approach, strains that are relatively low producers of endotoxin (lipopolysaccharide, LPS) are used so as to avoid the need to remove endotoxin from the final preparation prior to use in humans. For example, the vesicles can be prepared from Neisserial mutants in which lipooligosaccharide or other antigens that may be undesirable in a vaccine (e.g. Rmp) is reduced or eliminated.

Vesicles can be prepared from N. meningitidis strains that contain genetic modifications that result in decreased or no detectable toxic activity of lipid A. For example, such strain can be genetically modified in lipid A biosynthesis (Steeghs et al. Infect Immun 1999; 67:4988-93; van der Ley et al. Infect Immun 2001; 69:5981-90; Steeghs et al. J Endotoxin Res 2004; 10:113-9; Fissha et al, Infect Immun 73:4070, 2005). The immunogenic compositions may be detoxified by modification of LPS, such as downregulation and/or inactivation of the enzymes encoded by lpxL1 or lpxL2, respectively. Production of a penta-acylated lipid A made in lpxL1 mutants indicates that the enzyme encoded by lpxL1 adds the C12 to the N-linked 3-OH C14 at the 2' position of GlcN II. The major lipid A species found in lpxL2 mutants is tetra-acylated, indicating the enzyme encoded by lpxL2 adds the other C12, i.e., to the N-linked 3-OH C14 at the 2 position of GlcN I. Mutations resulting in decreased (or no) expression of these genes (or decreased or no activity of the products of these genes) result in altered toxic activity of lipid A (van der Ley et al. 2001; 69:5981-90). Tetra-acylated (lpxL2 mutant) and penta acylated (lpxL1 mutant) lipid A are less toxic than the wild-type lipid A. Mutations in the lipid A 4'-kinase encoding gene (lpxK) also decreases the toxic activity of lipid A. Of particular interest for use in production of vesicles (e.g., MV or OMV) are N. meningitidis strains genetically modified so as to provide for decreased or no detectable functional LpxL1-encoded protein. Such vesicles provide for reduced toxicity as compared to N. meningitidis strains that are wild-type for LPS production, while retaining immunogenicity of the fHbp and/or the JAR 4 epitope-containing peptide described in the present disclosure.

LPS toxic activity can also be altered by introducing mutations in genes/loci involved in polymyxin B resistance (such resistance has been correlated with addition of aminoarabinose on the 4' phosphate of lipid A). These genes/loci could be pmrE that encodes a UDP-glucose dehydrogenase, or a region of antimicrobial peptide-resistance genes common to many enterobacteriaciae which could be involved in aminoarabinose synthesis and transfer. The gene pmrF that is present in this region encodes a dolicol-phosphate manosyl transferase (Gunn J. S., Kheng, B. L., Krueger J., Kim K., Guo L., Hackett M., Miller S. I. 1998. Mol. Microbiol. 27: 1171-1182).

Mutations in the PhoP-PhoQ regulatory system, which is a phospho-relay two component regulatory system (e.g., PhoP constitutive phenotype, PhoPc), or low $Mg^{2+}$ environmental or culture conditions (that activate the PhoP-PhoQ regulatory system) lead to the addition of aminoarabinose on the 4'-phosphate and 2-hydroxymyristate replacing myristate (hydroxylation of myristate). This modified lipid A displays reduced ability to stimulate E-selectin expression by human endothelial cells and TNF secretion from human monocytes.

Polymyxin B resistant strains are also suitable for use, as such strains have been shown to have reduced LPS toxicity (see, e.g., van der Ley et al. 1994. In: Proceedings of the ninth international pathogenic *Neisseria* conference. The Guildhall, Winchester, England). Alternatively, synthetic peptides that mimic the binding activity of polymyxin B may be added to the antigenic compositions to reduce LPS toxic activity (see, e.g., Rustici et al. 1993, Science 259:361-365; Porro et al. Prog Clin Biol Res. 1998; 397:315-25). Endotoxin can also be reduced through selection of culture conditions. For example, culturing the strain in a growth medium containing 0.1 mg-100 mg of aminoarabinose per liter medium provides for reduced lipid toxicity (see, e.g., WO 02/097646).

In view of the above, exemplary antigenic compositions include one or more of the JAR 4 epitope-containing peptides of the present disclosure together with recombinant vaccines that include an fHbp or fragment thereof where the fHbp or fragment thereof may be provided as an isolated protein and/or may be provided in a vesicle vaccine. The various components described herein that may be included in an antigenic composition of the present disclosure may be combined together in vitro, ex vivo, and/or be already provided by the host cells used in the subject method. One of ordinary skill in the art may make the combination using any method of choice.

In another example, the antigenic compositions can include components of the "r3C" vaccine, which contains a recombinant fHbp v.1 (encoded by gene from strain MC58), GNA2132 (encoded by gene from strain NZ98/254), and NadA (encoded by the gene from strain 2996). In certain embodiments, the vesicles may be combined with the 5 component recombinant protein vaccine (5C or r5CV). The 5 component recombinant protein vaccine (r5Cv) refers to a recombinant protein vaccine containing GNA2091 fused with fHbp v. 1, GNA2132 (from NZ98/254) fused with GNA1030, and NadA and is described in Giuliani et al. (*Proc Natl Acad Sci USA* 2006; 103:10834-9).

Immunization

The JAR 4 epitope-containing peptides described herein can be generally administered in an immunogenic composition to a human subject that is at risk of acquiring a Neisserial disease so as to prevent or at least partially arrest the development of disease and its complications. An amount adequate to accomplish this is defined as a "therapeutically effective dose." Amounts effective for use will depend on, e.g., the immunogenic composition, the manner of administration, the weight and general state of health of the patient, and the judgment of the prescribing physician. Single or multiple doses of the immunogenic compositions may be administered depending on the dosage and frequency required and tolerated by the patient, and route of administration.

The peptides described herein are generally administered in an amount effective to elicit a humoral immune response in the host. As noted above, amounts for immunization will vary, and can generally range from about 1 μg to 100 μg per 70 kg patient, usually 5 μg to 50 μg/70 kg. Substantially higher dosages (e.g. 10 mg to 100 mg or more) may be suitable, and may be administered parenterally (e.g., by injection or topical administration) or by oral or nasal routes. The initial administration can be followed by booster immunization of the same of different polypeptide-containing antigenic composition. Usually vaccination involves at least one booster, more usually two boosters.

In general immunization can be accomplished by administration by any suitable route, including administration of the composition orally, nasally, nasopharyngeally, enterically, topically, transdermally, subcutaneously, intramuscularly, in tablet, solid, powdered, liquid, aerosol form, locally or systemically, with or without added excipients as may be suitable for the desired route of administration. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

An immune response can be assessed by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like).

In one embodiment, the antigenic compositions can be administered to a human subject, which subject may be immunologically naive with respect to *Neisseria meningitidis*. In a particular embodiment, the subject is a human child about five years or younger, and preferably about two years old or younger, and the antigenic compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

It may be generally desirable to initiate immunization prior to the first sign of disease symptoms, or at the first sign of possible or actual exposure to infection or disease (e.g., due to exposure or infection by *Neisseria*).

Kits

Also provided by the subject invention are kits for using the compositions disclosed herein and for practicing the methods, as described above. The kits may be provided for administration of a vaccine (e.g., prophylactic or therapeutic) against *N. meningitidis*. The kit can include one or more of the peptides disclosed herein, which may be provided in a sterile container, and can be provided in formulation with a suitable a pharmaceutically acceptable excipient for administration to a subject. The peptides can be provided with a formulation of an anti-*N. meningitidis* vaccine that provides for production of anti-fHbp antibodies (e.g., a formulation containing recombinant fHbp, vesicles from an fHbp-expressing strain, and the like), where the peptides of the present disclosure may be formulated separately or in combination with such vaccine.

In addition to above-mentioned components, the kits can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Materials and Methods

The following methods and materials were used in the Examples below.

Gene cloning. Wild-type fHbp genes were amplified from genomic DNA by PCR and cloned into pGEM-T-Easy (Promega). The resulting plasmids were treated with the restriction enzymes NdeI and XhoI and the approximately 800 base-pair fragments containing the fHbp coding sequences were ligated into pET21b (Novagen) cut with the same two enzymes. The plasmid clones were confirmed by DNA sequence determination of PCR products obtained by the amplification of the plasmid with primers specific for the T7 promotor and terminator regions. The plasmids encoded the full-length fHbp proteins except for the amino-terminal 19 amino acid signal sequence and 7 presumably flexible N-terminal residues, and included a C-terminal hexa-histidine ($His_6$) tag originating from the pET21b plasmid.

Site-Specific Mutagenesis.

Site-specific mutagenesis was used to test the role of amino acid residues involved in the JAR 4 anti-fHbp mAb epitope. Mutagenesis was performed using the QuikChange II kit (Stratagene) using 10 ng of plasmid template and the manufacturer's protocols. For testing residues putatively involved in mAb epitopes, mutagenesis reactions were performed on pET21-based plasmids encoding a wild-type fHbp gene. Site-specific mutagenesis was used to introduce the H26A and K27A substitution into the pET21 plasmid encoding v.1 fHbp from MC58. Mutant fHbp genes were confirmed by DNA sequencing as described for the wild-type plasmids, above.

fHbp Expression and Purification.

Wild-type and mutant fHbps were expressed in *Escherichia coli* BL21(DE3) (Novagen). fHbp purifications were performed from 1 L cultures. Mid-exponential cultures (optical density at 600 nm of 0.5-0.6) were grown at 37° C., induced with 0.5 mM isopropylthiogalactoside for 3-4 h and the bacteria harvested by centrifugation. The cells were lysed by incubation with chicken egg white lysozyme (Sigma) and two freeze/thaw cycles. Bacterial lysates were treated with DNase and RNase (Sigma) and protease inhibitors (Complete EDTA-free, Roche) and clarified by centrifugation at 13,000×g. Recombinant fHbps were purified by nickel chelate chromatography using Ni-NTA agarose (Qiagen) and buffers recommended by the supplier. Fractions containing purified fHbp were pooled and dialyzed against PBS (Roche) containing 5% (w/v) sucrose and 0.01% $NaN_3$, filter sterilized and stored at 4° C.

Direct-Binding and ELISA.

Binding of the mAbs to recombinant fHbp was measured by ELISA. The wells of a microtiter plate (Immulon 2B; Thermo Electron Corp.) were coated with 1 11 g/ml of recombinant fHbp in PBS and incubated overnight at 4° C. The plates were blocked with PBS containing 0.1% TWEEN-20 (Sigma) (PBST) and 1% BSA (Sigma). The primary antibodies were anti-fHbp mAbs (0.016 to 5 11 g/ml) and the secondary antibody was rabbit anti-mouse IgG-alkaline phosphatase (Invitrogen; 1:5,000), each diluted in PBST. After 1 h at room temperature, alkaline phosphatase substrate (Sigma) was added and the absorbance at 405 nm was measured after 30 min.

The ability of anti-rfHbp Abs to bind to the surface of live *N. meningitidis* was determined by flow cytometric detection of indirect fluorescence assay, performed as described previously (Granoff, D. M., et al. (1998) *J. Immunol.* 127:1011, and Moe, G. R., et al., (1999) *Infect. Immun.* 67:5664). FITC-conjugated $F(ab')_2$ goat anti-mouse IgG (H+L) (Jackson ImmunoResearch Laboratories, West Grove, Pa.) was the reagent used for fluorescence labeling. Different dilutions of serum pools from control mice immunized with adjuvant alone were used as negative controls.

Inhibition of Binding of Factor H.

The ability of an anti-fHbp mAb to inhibit binding of fH to fHbp was measured by ELISA. Wells of a microtiter plate were coated with rfHbp as described above. Dilutions containing 0.016 to 50 µg/ml of the mAb were added to the wells together with 50 µg/ml purified fH (Complement Technology, Inc.). The plates were incubated overnight at 4° C. Bound fH was detected with goat polyclonal anti-fH (Bethyl Laboratories) (1:1000) followed by mouse anti-goat IgG alkaline phosphatase conjugate (Santa Cruz Biotech) (1:2000). Both steps were performed at room temperature for 2 hours. After washing, substrate was added and developed as described above for the antibody binding ELISA.

Binding of Factor H to N. Meningitidis.

The bacterial suspension (90 µl) was incubated for 10 or 30 mM at 37° C. with 10 µl NHS, or 10 µl HIS, or 5 µg purified fH (1 mg/ml in PBS). Suspensions were centrifuged at 10,000 g for 2 min and pellets were washed once with HBSS before adding anti-fH antibody used for detecting fH surface-bound fH was monitored by the addition of affinity-purified polyclonal rabbit anti-fH (final dilution of 1:100 of a 0.26 mg/ml stock solution) for 30 min at room temperature, followed by FITC-labeled anti-rabbit IgG (Sigma Chemical Co.; final dilution of 1:100). The bacteria were resuspended in 1 ml HBSS and applied to a fluorescence-activated cell sorter (FACScan®, Becton Dickinson Immunocytometry Systems, San Jose, Calif.) and 50,000 events were counted.

Western Blotting.

One ml of bacterial culture was grown and induced as described above (see fHbp expression and purification, above). The cells were harvested by centrifugation and were resuspended in 0.5 ml of 1×LDS sample buffer (Invitrogen) containing 25 mM 2-ME. Bacterial lysates were separated by SDS-PAGE using 4-12% NuPAGE polyacrylamide gels and MES SDS-PAGE buffer (Invitrogen). Proteins were transferred to polyvinylidene difluoride (PVDF) membranes (Immobilon-P; Millipore). The membranes were blocked using PBST containing 2% nonfat dry milk (Carnation). The membranes were washed, incubated with the different anti-fHbp mAbs (1 to 5 µg/ml) or, as a control for protein expression by the different clones, 0.02 µg/ml of Penta-His mAb (Qiagen). The membranes were washed in PBST and incubated with a 1:10,000 dilution of a rabbit anti-mouse IgG-horseradish peroxidase conjugate (Zymed) and washed again. The membranes were developed with a chemiluminescent substrate (ECU$^+$; GE Healthcare) and visualized on a Storm 840 imager (Molecular Dynamics).

Bactericidal Activity.

Complement-mediated bactericidal activity was measured as described previously using washed, log-phase bacteria grown in Mueller-Hinton broth supplemented with 0.25% glucose and 0.02 mM CMP-NANA to an $OD_{620}$ of 0.6 (17). The buffer was Dulbecco's phosphate buffered saline (Mediatech, Inc.) containing 0.9 mM $CaCl_2 \times 2\ H_2O$, 0.5 mM $MgCl_2 \times 6\ H_2O$ and 1% (w/v) BSA. The complement source was human serum from a healthy adult with no detectable intrinsic bactericidal activity. For synergism of mAb bactericidal activity, equal quantities of two mAbs ranging from 0.4 to 50 ug/ml (final concentration) were used. The bactericidal activity ($BC_{50}$) of the mouse antiserum (or mAb combination) was defined by the dilution (or mAb concentration) that gave a 50% decrease in the number of CFU after 60 mM incubation at 37° C. as compared with the CFU at time 0 in the negative control reactions.

Activation of Human Complement Deposition on the Surface of Live Encapsulated Meningococci.

Anti-fHbp Ab-dependent deposition of C3b or iC3b on the bacterial surface of live N. meningitidis bacteria was determined by flow cytometry, performed as previously described (Welsch, J. A. et al. (2003) J. Infect. Dis. 188:1730). Complement deposition on the bacterial surface was detected with FITC-conjugated sheep anti-human C3c (BioDesign, Saco, Me.), which reacts with both C3b and iC3b. The complement source was serum from a healthy adult with no detectable intrinsic bactericidal activity, and no detectable group B or C anticapsular Ab when tested by ELISA. In the absence of added Ab, this serum gave no detectable deposition of complement on the bacterial surface of different strains. Positive and negative controls were those described above for measurement of Ab binding by flow cytometry.

Complement-Dependent Bactericidal Ab Activity.

After overnight growth on chocolate agar, several colonies of N. meningitidis were inoculated into Mueller-Hinton broth (starting $A_{620\ nm}$ of about 0.1) and the test organism was grown for about 2 h to an $A_{620\ nm}$ of about 0.6. After washing the bacteria twice in Gey's buffer, ~300-400 CFU were added to the reaction mixture. The assays were performed with human complement (described above) and, in selected experiments, were also performed with rabbit complement (pooled infant rabbit serum obtained from Cedarlane Laboratories, Hornby, Ontario, Canada). The final reaction mixture of 60 µl contained 20% (v/v) complement, and serial 2-fold dilutions of test sera or mAbs diluted in Gey's buffer. CFU/ml in the reaction mixtures was determined after overnight growth on chocolate agar (Remel, Rancho Cordova, Calif.). Bactericidal titers or concentrations were defined as the serum dilution (or Ab concentration), resulting in a 50% decrease in CFU/ml after 60-min incubation of bacteria in the reaction mixture, compared with the control CFU/ml at time 0. Typically, bacteria incubated with the negative control Ab and complement showed a 150-200% increase in CFU/ml during the 60 min of incubation.

Phage Library Preparation and Screening.

Peptides binding to JAR4 mAb were selected by panning four different phage libraries: pVIII-9aa, pVIII-9aa.Cys, pVIII-12aa and pVIII-Cys.Cys. All libraries have been constructed in the pVIII two-gene/phagemid vector pC89 (Felici et al. J Mol. Biol. 222 (1991) 301-310) by cassette mutagenesis. The libraries carried random inserts encoding peptides of various sizes fused into the N-terminal region of the major coat protein (protein VIII) of filamentous phage. The two different libraries referred to as pVIII-9aa and pVIII-12aa were composed of random 9-mers and 12-mers, respectively, whereas the libraries referred to as pVIII-9aa.Cys and pVIII-Cys.Cys were libraries in which the random insert contains two cysteine residues. In the latter libraries, cysteines promote the formation of a disulfide bridge that constrains to some extent the conformation of the displayed peptide (Luzzago et al. (1997) "Construction of disulfide-constrained random peptide libraries displayed on phage coat protein VIII." In: Methods in Molecular Biology. Combinatorial peptide library protocols. S. Cabilly, Ed. Vol. 87, pp. 155-164. Humana Press, Totowa, N.J.).

Specific phage clones were isolated from the libraries by two rounds of affinity selection. In the first round the monoclonal antibody was incubated at 4° C. overnight at 1 µM concentratin with $10^{10}$ transducing units of library in a total volume of 10 µl. The mixture of library and antibody was then incubated with magnetic beads conjugated with protein G (100 µl, protein G-DYNABEADS®, Dynal, Norway) for 1 hour at room temperature under agitation. The beads were washed 10 times with 1 ml of washing solution (PBS, 1% TRITON). The bound phage pools were eluted with 100 µl of 0.1 M HCl, pH 2.2 adjusted by glycine, neutralized with 10 µl of 2M Tris, pH 9.6 and amplified by infecting bacterial strain DH5αF' (supE44 DlacU169 (f80 lacZDM15) hsdR17 recAl endAlgyrA96 thi-1 relAl F' [traD36 proAB+laciqlacZDM15]). The second round of biopanning was carried out in the same way, but using $10^{10}$ transducing units from first round amplified phage pools. Positive phage clones were identified through immunoscreening (Luzzago et al. Gene. 128 (1993) 51-57.).

Phage obtained from the affinity selection were mixed with 2 ml of a culture of XL1-blue cells (recA1 endA1 gyrA96 thi hsdR17 (rK-mK+) supE44 relA1 lac-[F' proA+B+lacIq lac-ZΔM15 Tn10]) (A600~0.8). After one hour of incubation at 37° C., the mixture was plated on Petri dishes containing LB agar plus 50 mg Ap/ml. After overnight incubation the colonies were scraped from the plates and sufficient cells were added to 10 ml of LB broth with 100 mg Ap/ml, to give an A600 of 0.05. The culture was incubated at 37° C. until the A600 was 0.22; 1 ml was superinfected with M13KO7 helper phage ($10^{10}$ phage particles), incubated 15 min at 37° C. without shaking, and then centrifuged 2 min in an Eppendorf centrifuge at maximum speed. To eliminate the excess of helper phage the pellet was washed three times with LB broth and finally resuspended in 1 ml of LB broth. A 10 µl portion was diluted with 1 ml of LB broth and 100 µl aliquots were mixed with 500 µl of an overnight culture of XL1-blue cells and 12 ml of BBL Top Agar and poured on LB Agar plates (15 cm diam.). After 5 h of incubation at 37° C., nitrocellulose filters were applied on the plates and left overnight at 37° C. Filters were blocked for 1 h with PBS/5% non-fat dry milk/0.05% NP40. Filters were incubated for 2 h at room temperature with the primary mAb (JAR4) at a final concentration of 1 mg/ml in blocking solution, then for 1 hour at room temperature with anti-mouse IgG Ab conjugated to alkaline phosphatase (Promega, Madison, Wis., USA; working dilution ⅛₀₀₀) in the same solution. The reaction was revealed with nitro-blue-tetrazolium and 5-bromo-4-chloro-3-indolyl-phosphate.

Detection of the Reactivity of the Phage Library Clones with the mAb.

Binding of JAR4 to peptides described herein (e.g., as displayed in the phage library-selected clones) was also measured by two ELISA methods, referred to as "SEPHELISA" and "PHAGELISA".

SEPHELISA—Ninety-six wells plates were coated o.n. at 4° C. with 100 µl per well of a rat anti-pili (coat protein III) monoclonal antibody (concentration 1 mg/ml) in 50 mM NaHC03, 0.02% (w/v) NaN3, pH 9.6, and washed 8 times with TBST (50 mM Tris/Cl, 150 mM NaCl, pH 7.5, 0.05% (v/v) TWEEN 20). One hundred µl per well of cleared phage supernatant was added. After washing as above and incubation with antibody (concentration 1 mg/ml) in blocking buffer (5% (w/v) non-fat dry milk, 0.05% TWEEN 20 in PBS), and washing, the binding of the monoclonal antibody was detected by alkaline-phosphatase conjugated goat anti-mouse IgG antibody (Sigma, dilution 1:5000) using p-nitrophenyl phosphate substrate tablets (Sigma). The absorbance at 405 nm was measured after 30 min.

PHAGELISA—Aliquots in 96 wells ELISA plates 100 µl per well of JAR4 mAb were diluted (1 µg/ml) in 50 mM NaHC03, 0.02% (w/v) NaN3, pH 9.6 and incubated 3 hrs at 37° C. or overnight at 4° C. After washing 8 times with 1×PBS containing 0.05% (v/v) TWEEN 20), 200 µl of blocking buffer (PBS, 0.05% TWEEN 20, 5% non-fat dry milk) was added and incubated for 1 hr at 37° C. The wash was discarded and a mixture of 100 µl cleared phage supernatant and 100 µl blocking buffer was added, to the plate and incubated for 3 hrs at 37° C. or overnight at 4° C. After washing 8 times with 1×PBS containing 0.05% (v/v) TWEEN 20), and anti-M13 peroxidase conjugate antibody (Amersham Biosciences, Buckinghamshire, UK) was added at a dilution of 1:15000 in blocking buffer (100 µl/well) and incubated for 1 h at 37° C. After further washing, antibody binding was detected by adding TMB substrate, incubated for 45 min at room temperature and stopped with 25 ml of 1 M H2SO4 and reading absorbance at 450 nm.

Example 1

Binding Specificity of JAR 4 mAb with Variants of fHbp

Several murine monoclonal antibodies (mAbs) prepared against recombinant proteins representative of the three major variant groups of factor H binding protein (fHbp) were used. These variant groups are designated variant 1 ("v.1"; Welsch et al. *J Immunol* 2004; 172:5606-15), variant 2 ("v.2", Beernink et al. *J Infect Dis* 2007; 195:1472-9) and variant 3 ("v.3"). A summary of the mAbs available for use is presented in FIG. 2. The examples below characterize JAR 4 antibody in its binding to variants of fHbp, its cooperativity in eliciting bactericidal activity, and its epitope on fHbp. Epitopes recognized by each of these "JAR" mAbs are surface-exposed on encapsulated meningococcal strains and capable of interacting with protective antibodies.

For convenience, the protein has been divided into three domains, designated A, B and C (Giuliani et al. *Infect Immun.* 2005; 73:1151-60). As discussed above, the A domain is highly conserved between variant groups 1 and 2, whereas the B and C domains contain sequences that diverge among strains from different variant groups (Note that the convention of numbering amino acid residues beginning with the first residue after the signal sequence is adopted herein). FIG. 1 provides a schematic of the domains of an exemplary fHbp.

Binding of JAR 4 and JAR 5 mAbs was investigated by ELISA. Notably, JAR 5 binds to v.1 or subvariants of v.1 fHbp expressed by strains MC58, 4243, M1390, and NZ98/254 (Welsch et al. *J Immunol* 2004; 172:5606-15).

The results of evaluation of binding of the JAR 5 and JAR 4 mAbs to v.1, v.2, and v.3 fHbp is provided in FIG. 3, panels A and B. For JAR 5, the concentrations of mAb that resulted in an ELISA $OD_{405}$=0.5 were 0.001 µg/ml, >50 µg/ml, and >50 µg/ml for v.1, v.2, and v.3, respectively. Similar to JAR 5, JAR 4 also binds strongly with v.1 fHbp with a concentration of 0.003 µg/ml conferring an $OD_{405}$ of 0.5. Different from JAR 5, however, JAR 4 cross-reacted with the v.2 fHbp recombinant protein (0.05 µg/ml of the mAb gave an $OD_{405}$=0.5), and also gave a weak reaction with the v.3 recombinant protein (50 µg/ml gave an $OD_{405}$=0.16, 3-fold above background). Although JAR 4 cross-reacted strongly by ELISA with the v.2 rfHbp encoded by the gene from strain 2996, this mAb induced no detectable level of bactericidal activity, binding, or activation of C3b deposition on the surface of live bacteria from strain 2996 or two other group B strains expressing fHbp v.2 proteins (strains M986 and 8047) (data not shown).

Example 2

Inhibition of Binding of Factor H to *N. Meningitidis* by Anti-fHbp mAb

*N. meningitidis* is known to bind factor H (fH), the negative regulator of the alternative pathway of complement activation, to promote their survival in a host. The ability of several mAbs to selectively inhibit binding of fH to intact bacteria was then investigated using flow cytometry.

Figure 4:
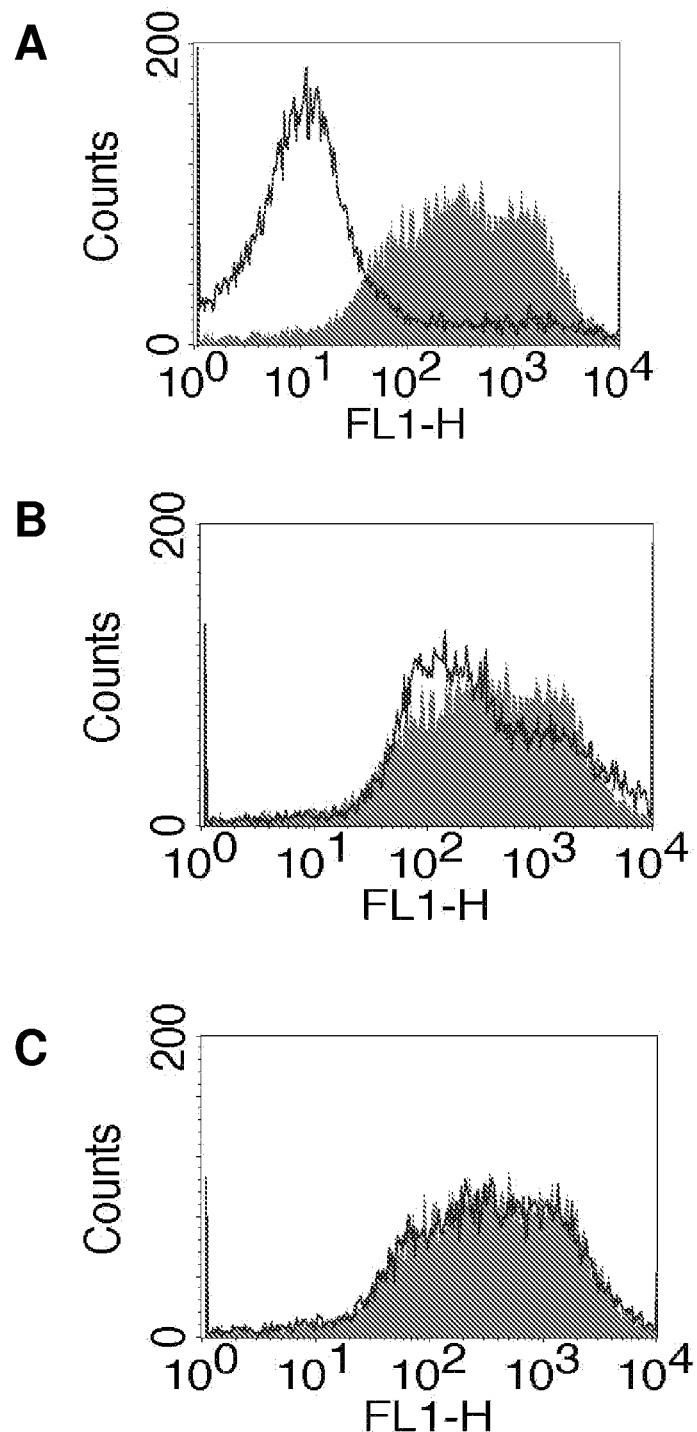
FIG. 4 is a series of graphs showing the ability of JAR 5, Anti-P1.7, and JAR 4 mAbs to inhibit the binding of fH to *N. meningitidis* strain H44/76 by flow cytometry. Filled areas represent populations treated with negative control sera. Panel A, Inhibition of binding of fH by JAR 5. Panel B, Binding of fH in the presence of Anti-P1.7 (an anti-PorA antibody, control). Panel C, Binding of fH in the presence of JAR 4.

As assessed by binding of fH to a v.1 strain H44/76 of *N. meningitidis* investigated using protocols previously described (Ram S et al. (1998) *J. Exp. Med.* 187:743-752), the anti-fHbp mAbs, JAR 1, 3, and 5 block binding of fH to intact bacteria (FIG. 4, panel A). A negative control, anti-PorA mAb, anti-P1.7, was used, which did not block fH binding to strain H44/76, but did bind to the strain (FIG. 4, panel B). JAR 4, however, did not block fH binding to strain H44/76 (FIG. 4, panel C) although it does bind to v.1 fHbp, as shown in FIG. 2. From these results, it was found that JAR 4 alone was not able to prevent the binding of fH to the bacteria.

Example 3

Anti-fHbp mAb Bactericidal Activity

Each of JAR 1, JAR 3, and JAR 4 was previously shown to possess bactericidal activity against group B strain MC58 when administered alone (Welsch J A et al. (2004) *J. Immunol.* 172:5606). JAR 5, however, failed to show any detectable bactericidal activity against MC58. Although strain NZ98/254 has an fHbp with substantial amino acid sequence identity to the fHbp of MC58, none of the tested mAbs was found to be strongly bactericidal against NZ98/254. One notable characteristic of NZ98/254 is that it is a low fHbp-expressing strain relative to other *N. meningitidis* strains such as H44/76.

To further investigate the bactericidal activity of the various mAbs, survival of *N. meningitidis* strain NZ98/254 after incubation for 60 min at 37° C. in the presence of different concentration of mAbs was measured. This experiment was carried out as described above in the presence of 20% human complement. The mAbs tested included JAR 3, JAR 4, JAR 5, a combination of JAR 4 and JAR 5, and a positive control mAb P1.4.

Figure 5:
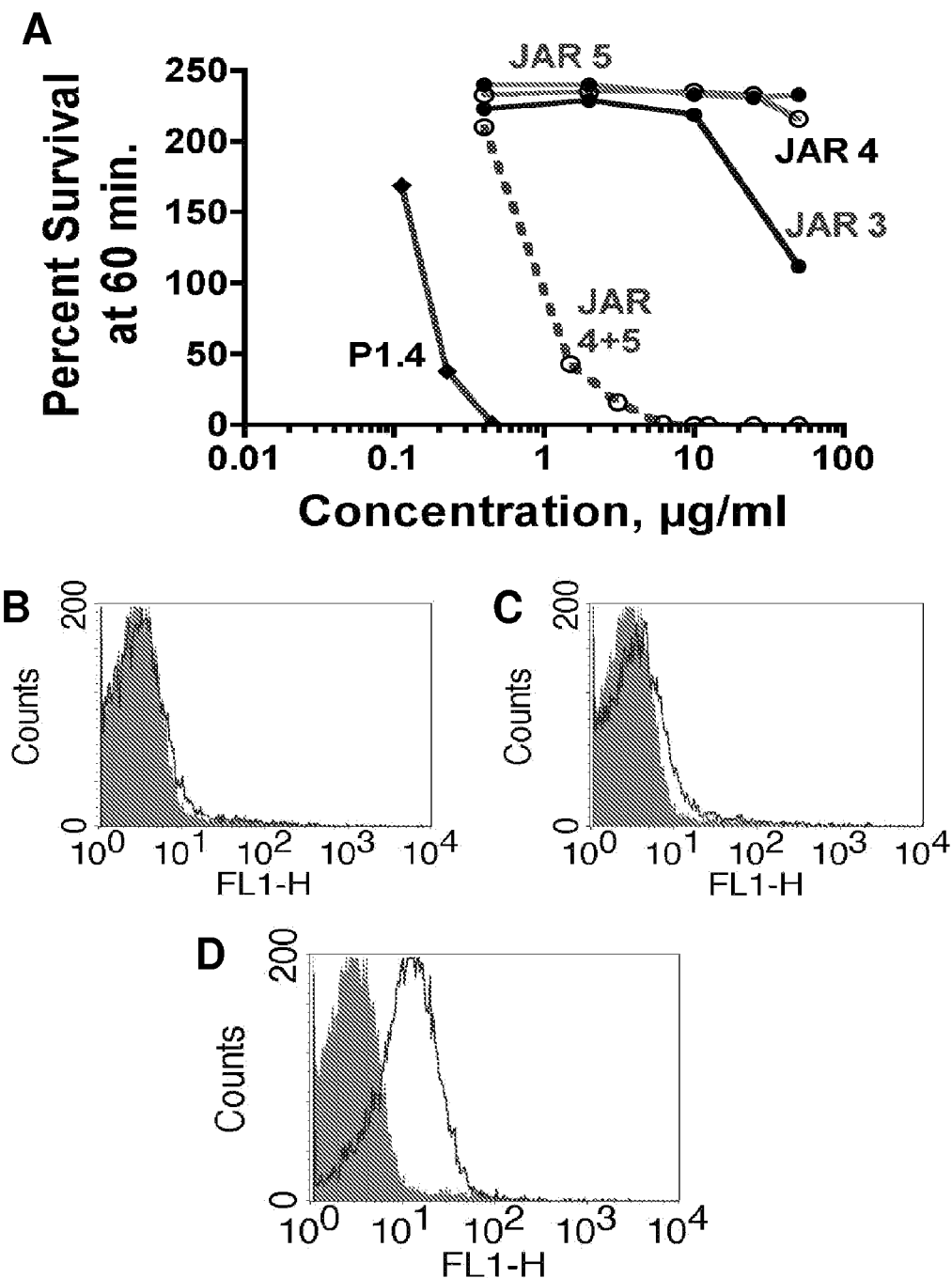
FIG. 5, panel A graphs the survival of *N. meningitidis* group B strain MC58 after incubation for 60 min at 37° C. in the presence of different concentrations of various JAR mAbs or anti-PorA P1.4 and 20% human complement.

As presented in FIG. 5, panel A, JAR 3 showed minimal bactericidal activity against the strain NZ98/254. JAR 4 and JAR 5 also showed no significant bactericidal activity against strain NZ98/254. However, a combination of JAR 4 and JAR 5 exhibited strong bactericidal activity against strain NZ98/254.

In addition to measuring the survival of *N. meningitidis*, complement activation may also be assessed by measuring complement component (C4) on live encapsulated *N. meningitidis*. A high level of C4 bound on encapsulated *N. meningitidis* indicates that a classic component pathway was actively involved where a pathogen was marked for bactericidal activity and/or ingestion and destruction by a phagocyte.

To determine the level of C4 binding on NZ98/254, flow cytometric detection of indirect immunofluorescence was used in accordance with the methods described above. The results of this analysis are shown in FIG. 5, panels B, C, and D. The filled area in each panel represents the negative control, where a population was treated with complement plus negative control serum. The open area in FIG. 5, panel B indicates binding of C4 with test antiserum containing JAR 4 at 50 µg/ml. FIG. 5, panel C shows the binding of C4 with test antiserum containing JAR 5 at 50 µg/ml. When the test antisera of a combination of JAR 4 and JAR 5 at 2 µg/ml was used, as shown in FIG. 5, panel D, there was a significant shift in the population of cells toward increased fluorescence, a sign of a higher level of C4 bound on *N. meningitidis* strain NZ98/254.

The results obtained with the percent survival of *N. meningitidis* and with the binding of C4 on *N. meningitidis* are provided in Table 1 below. A strong synergistic bactericidal activity of a JAR 4 and JAR 5 combination is observed, as well as in the JAR 4 JAR 3 combination (JAR 3 and JAR 5 exhibit binding to the same or overlapping epitope). Moreover, JAR 4 also exhibited synergy in bactericidal activity with the JAR 11 and JAR 13 mAb. Thus, the ability of JAR 4 to activate the classic component pathway on even low fHbp v.1 or v.2-expressing strains is enhanced when combined with another mAb.

TABLE 1

Cooperative Anti-fHbp JAR 4 mAb Bactericidal Activity (human complement)

| JAR 4 mAb Pair | Strain (fHbp v. group) | Combination BC$_{50}$, µg/ml |
| --- | --- | --- |
| mAb 502 | H44/76 (v.1) | 1 |
| JAR 3 | NZ98/254 (v.1) | 1 |
| JAR 5 | NZ98/254 (v.1) | 2 |
| JAR 11 | 8047 (v.2) | 5 |
| JAR 13 | 8047 (v.2) | 4 |
| JAR 10 | NZ98/254 (v.1) | >50 |
| JAR 10* | 8047 (v.2) | >50 |

*JAR 10 is bactericidal against strain 8047 when tested with JAR 11 (IgG2,)

Example 4

Identifying Peptides Expressing a JAR 4 Epitotpe

As illustrated above, binding of an antibody to the JAR 4 epitope provides for synergy in bactericidal activity of other anti-fHbp antibodies. Thus, identification of peptides that can be used in a vaccine to elicit antibodies that share fHbp epitope binding properties of JAR 4 is of interest.

In order to identify peptides useful in eliciting antibodies having the eptitope-binding properties of the JAR 4 mAb, libraries of filamentous bacteriophage containing random peptides (9-mers and 12-mers) fused to protein VIII were screened using the JAR 4 mAb as described above. Phage eluted in the final step were used to infect host bacteria, from which the phagemids were collected and the relevant DNA sequence amplified by PCR and sequenced to identify the peptides that interacted with JAR 4 mAb. The relative binding affinity of the peptide of the isolated phage was determined by both PHAGELISA and SEPHELISA, as described above.

Table 2 below provides the details of the results.

| CLONE | CLONE INFO | PHAGELISA | SEPHELISA | SEQUENCE | SEQ ID NO |
| --- | --- | --- | --- | --- | --- |
| 1 | 5 mix JAR 4 = 2 JAR 4 = 4 JAR 4 = 5 JAR 4 = 6JAR 4 | +++ | ++++ | H D H K L E G T E | 14 |

-continued

| CLONE | CLONE INFO | PHAGEL ISA | SEPHEL ISA | SEQUENCE | SEQ ID NO |
|---|---|---|---|---|---|
| 2 | 2 mix JAR 4 = 6 mix JAR 4 = 8 mix JAR 4 | ++ | ++++ | C G G V Y D D K T G C A | 15 |
| 3 | 1 9aa JAR 4 | ++++ | ++++ | H D H K T Q L D P | 16 |
| 4 | 3 mix JAR 4 = 9 mix JAR 4 | +++ | +++ | W T L A V F D H K A Q T | 17 |
| 5 | 13 mix JAR | + | ++ | G C M G Y D H R S G C V | 18 |
| 6 | 13 9aa JAR 4 | + | ++ | F H D H K T A N Q | 19 |
| 7 | 10 mix JAR 4 | + | ++ | W R W C G F E R C P E G | 20 |
| 8 | 19 mix JAR 4 | + | ++ | H D H R I W P L D V T A | 21 |
| 9 | 7 mix JAR 4 | + | + | N D E R Q M S D W Y R A | 22 |
| 10 | 1 mix JAR 4 | + | + | H V H R G S Q G G Q R Q | 23 |
| 11 | 4 mix JAR 4 | + | + | L E W C G F S R C E V G | 24 |
| 12 | 11 mix JAR 4 | + | + | K D H R H M L W P E E S | 25 |
| 13 | 12 mix JAR 4 | + | + | L C Q E R L S Q R C G V | 26 |
| 14 | 14 mix JAR 4 | + | + | W V L C G Q G C G G T A | 27 |
| 15 | 15 mix JAR 4 | + | + | R C Q V Q M V L C A L | 28 |
| 16 | 16 mix JAR 4 | + | + | H D H K H G F Q E P A S | 29 |
| 17 | 17 mix JAR 4 | + | + | S D W G W G G R A E Q H | 30 |
| 18 | 18 mix JAR 4 | + | + | V G W C G F E R C S S A | 31 |

++++ = O.D. from 2 to 3.5
+++ = O.D. from 1 to 2
++ = O.D. from 0.5 to 1
+ = O.D. from 0.15 to 0.5

The sequences of the nucleic acid sequences encoding the above peptides are provided in FIG. 8.

Example 5

Analysis of Effect of Mutations in Dhk Sequence in Native fHbp

As illustrated above, the phage display studies identified several peptides that shared a tripeptide consensus sequence, DHK. This sequence aligned with residues 25-27 in the A domain of v.1, v.2, and v.3 fHbp (see FIG. 7, providing a partial sequence of the A domain of fHbp of v.1 and v. 3; v.1 and v.2 fHbp have the same amino acid sequence in this region). The role of the amino acids at residues 25, 26 and 27 in binding with JAR 4 was confirmed by constructing site-specific mutant recombinant fHbps and measuring their reactivity with JAR 4 by ELISA as described below.

Site-directed mutagenesis of residues 25, 26 and 27 was performed, each of which was individually changed to alanine in fHbp from the v.1 group (gene from MC58). These mutants were created using the non-signal containing sequence from strain MC58 (MVAAD . . . GLAAKQ) (SEQ ID NO:73), and are referred to as D25A, H26A and K27A, respectively. The amino acid sequences of the portions of the A domains of these mutants is provided in FIG. 7, Panel A.

Figure 6:
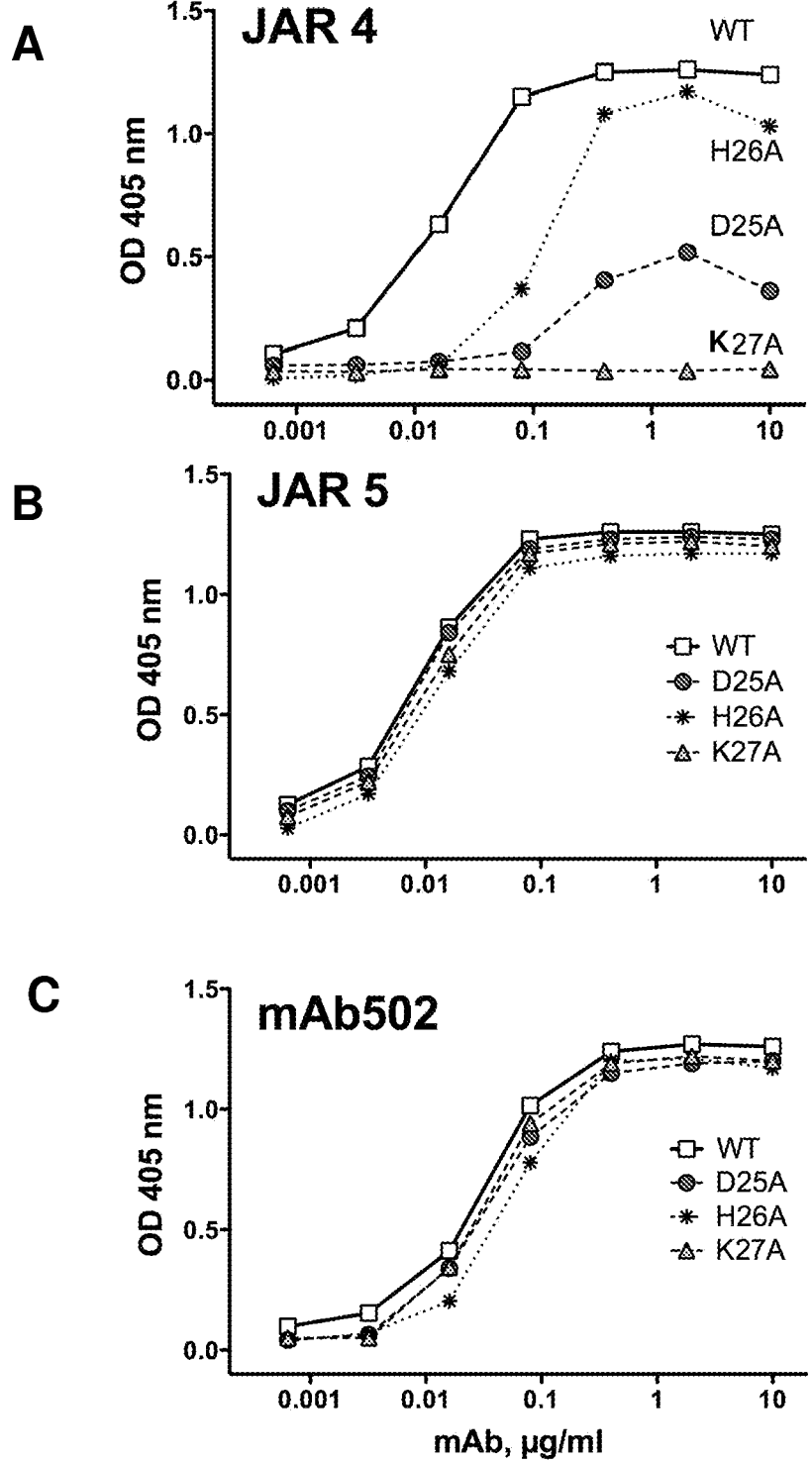
FIG. 6 presents a set of graphs illustrating the specificity of various mAbs in binding to purified, recombinant v.1 fHbp (gene cloned from strain MC58) (WT) and to v.1 fHbp with certain mutated residues. Binding to variants in which D25, H26 or K27 were mutated to alanine was compared to binding to the wild-type variant. Binding of anti-fHbp mAbs to fHbp by was measured by ELISA. Panel A, Binding of JAR 4 to various types of fHbp. Panel B, Binding of JAR 5 to various types of fHbp. Panel C, Binding of mAb 502, which is known to bind to C domain of v.1 fHbp, to various types of fHbp.

Results of the binding experiment between mutated fHbp and the various JAR mAbs are shown in FIG. 6.

As compared with the wild-type recombinant fHbp, the mutant containing the D25A substitution showed an approximately 1000-fold decrease in JAR 4-reactivity, whereas the H26A substitution showed an approximately 10-fold decrease in JAR 4 reactivity. The introduction of K27A eliminated detectable JAR 4 binding (FIG. 6, panel A). All three mutants showed identical concentration-dependent binding with two other mAbs, JAR 5 (FIG. 6, panel B) and mAb 502 (FIG. 6, panel C), which are specific for epitopes in the B and C domains, respectively.

As noted above, a protein sequence alignment of the regions containing residues 25-27 revealed that each of the v.1, v.2, and v.3 protein sequences contain DHK as residues 25-27 (FIG. 7, Panel B). However, JAR 4 does not detectably bind fHbp v.3. Since the tripeptide is conserved across fHbp in all three antigenic variant groups and JAR 4 reacts primarily with fHbp in the v.1 or v.2 groups, additional epitopes on the fHbp protein are likely involved in JAR 4 binding. As such, a region of the A domain containing the DHK tripeptide is necessary but not sufficient for expression of the JAR 4 epitope.

Moreover, the following two peptides from the native fHbp sequence showed no detectable binding to JAR 4 by ELISA.

ADALTAPLDHKDK(aa 42 to 54, v.1)    (SEQ ID NO: 32)

DHKDKGLQSLTLD(aa 50 to 62, v.1)    (SEQ ID NO: 33)

These data suggest that binding of JAR 4 to the peptide may require more than two amino acid residues C-terminal of the DHK motif. Notably, while the peptide of SEQ ID NO: 32 did not provide for detectable binding of JAR 4, the peptide of SEQ ID NO: 17, which contains a three amino acid residues positioned C-terminal to the DHK motif was bound by JAR 4. The data using SEQ ID NO: 33 suggest that the DHK tripeptide motif may not present an epitope recognized by JAR 4 when the tripeptide is positioned at the N-terminus of the peptide. Thus, peptides containing a DHK sequence may require that the N-terminal residue of the motif be modified so as not to contain an N-terminal amine (e.g., modified so as to be covalently bound to a moiety through the terminal amino group, e.g., such that at least one amino acid residue N-terminal to the motif).

Example 6

Analysis of Effect of Mutations in Dhk Sequence in Native fHbp

Mice were immunized with recombinant fHbp vaccines encoded by variant 1 genes from strains MC58, NM452 and NZ98/254 (Peptide ID numbers 1, 15 and 14, respectively), and variant 2 genes from strains 8047 and RM1090 (Peptide ID numbers 77 and 22, respectively). Three IP injections were given, each separated by 3 weeks. The vaccines were administered with Freund's complete adjuvant for the first injection and incomplete adjuvant for the second and third injections. Serum samples were obtained 3 weeks after the third injection and pooled (4 to 6 mice per pool). The anti-fHbp antisera were tested for human complement-mediated bactericidal activity in the presence or absence of JAR 4 at 40-50 or 10 µg/ml. A control mAb that reacted with the respective target strains also was tested for augmentation of bactericidal titers (JAR 5 for strains in the variant 1 group and JAR 31 for strains in the variant 2 group). The complement source was IgG-depleted human serum as previously described. The bactericidal ($BC_{50}$) titers were calculated as the serum dilutions resulting in a 50% decrease in CFU/ml after 60 min incubation at 37° C. as compared with the CFU/ml at time 0.

Table 3 shows the serum geometric mean bactericidal titers of the antisera tested alone, or with JAR 4 or a control mAb against three different test strains. When tested against strain H44/76 (fHbp in the variant 1 group), the addition of 10 or 50 µg/ml of JAR 4 augmented the bactericidal of the titer of antiserum from mice immunized with recombinant fHbp variant 1 from strain NM452 (peptide ID 15) by ~10 to 20-fold (reciprocal geometric mean titers [GMT] of 1183 and 2510 with JAR 4, respectively, compared with 122 without JAR 4). The addition of 50 µg/ml of a control anti-fHbp mAb JAR 5 augmented the titer by ~5-fold (1/GMT of 632). When tested against a second strain NZ98/254, the addition of 50 or 10 µg/ml of JAR 4 also gave augmentation of serum bactericidal activity (1/GMTs of 3562 and 1817, respectively, vs. 96 without added mAb, or 305 when 40 µg/ml of the control mAb, JAR 5). These data suggested that the polyclonal antisera elicited by the recombinant fHbp vaccine had less antibody directed at the JAR 4 epitope than the JAR 5 epitope, which is consistent with the fact that variant 1 vaccine antigen does not to express the epitope recognized by JAR 4. Against strain NZ98/254, the addition of JAR 4 to polyclonal antiserum from mice immunized with a homologous fHbp variant 1 vaccine (prepared from the gene from NZ98/254), which contained the JAR 4 epitope, also augmented the bactericidal titer (1/titer of 3162 as compared to 501 without JAR 4, or 1342 with JAR 5, Table 3). However, against strain NZ98/254 there was minimal augmentation by JAR 4 of the bactericidal activity of a third variant 1 antiserum from mice immunized with recombinant fHbp encoded by a gene from MC58 (peptide ID number 1) (Table 3).

Figure 9:
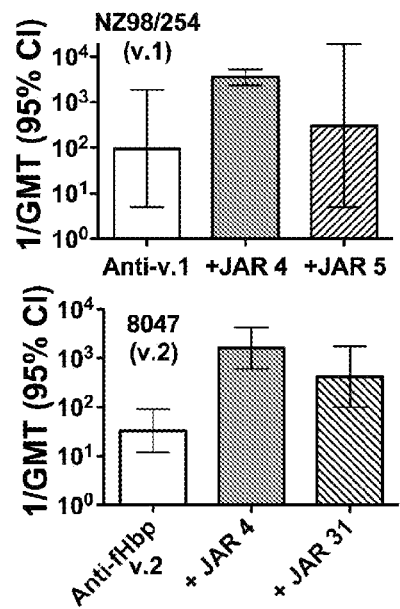
FIG. 9 presents graphs showing the augmentation of serum bactericidal activity by the addition of anti-fHbp mAb, JAR 4. Top panel, strain NZ98/254 (fHbp variant 1, peptide ID 14) and antiserum from mice immunized with recombinant fHbp encoded by a gene from strain Nm452 (variant 1, peptide ID 15). Bottom panel, strain 8047 (fHbp variant 2, peptide ID 77) and antiserum from mice immunized with recombinant fHbp encoded by a gene from strain RM1090 (variant 2, peptide ID 22). The data shown are for JAR 4 or the control mAbs tested at 40 µg/ml (See Table 3). The ID numbers are from the factor H binding protein database at the *Neisseria*.org web site (*neisseria*.org/perl/agdbnet/agdbnet.pl?file=nm_fhbp.xml).

The augmentation of anti-NM452 bactericidal titers against strain NZ98/254 is summarized in FIG. 9 (top panel). The bottom panel shows similar augmentation by JAR 4 (40 µg/ml) of bactericidal activity of antisera from mice immunized with a recombinant fHbp vaccine in the variant 2 group (gene from RM1090) when tested against strain 8047 (fHbp variant 2 group). Although the fHbp variant 2 vaccine expressed the JAR 4 epitope, the addition of JAR 4 (40 µg/ml) augmented the bactericidal titer (1/GMT of 1612 with JAR 4 vs. 33 without the mAb, or 419 with a control mAb, JAR 31). The addition of JAR 4 to an antiserum from mice immunized with a second recombinant fHbp variant 2 vaccine (encoded by a gene from strain 8047) also augmented bactericidal activity (1/GMT of 6250 with JAR 4 compared to 78 without JAR 4, and 1341 with a control anti-fHbp mAb, JAR 13). Collectively, these data underscore the ability of a mAb directed at the JAR 4 epitope to augment bactericidal activity of polyclonal anti-fHbp antibodies elicited by recombinant fHbp variant 1 or 2 vaccines. Further the augmented bactericidal titers were observed with antisera from mice immunized with recombinant fHbp variants that expressed the JAR 4 epitope (NZ98/254, 8047 or RM1090) or did not express the epitope (NM452) as long as the target strains expressed the epitope.

TABLE 3

Summary of augmentation of serum bactericidal titers by anti-fHbp mAb, JAR 4

| Strain (fHbp variant) | Anti-fHbp Antiserum | No. Pools | Antiserum alone | Antiserum + JAR 4 mAb | Antiserum + Control mAb¶ | JAR 4 mAb | Control mAb |
|---|---|---|---|---|---|---|---|
| H44/76 (v.1) | NM452 | 2 | 122 | 2510 (50 ng/ml) | 632 (JAR 5) | 20.6 | 5.2 |
|  | NM452 | 2 | NA** | 1183 (10 ng/ml) | ND* | 9.7 | ND* |
| NZ98/254 (v.1) | NZ98/254 | 1 | 501 | 3162 (40 ng/ml) | 1342 (JAR 5) | 6.3 | 2.7 |
|  | NM452 | 3 | 96 | 3516 (40 ng/ml) | 305 (JAR 5) | 36.6 | 3.2 |
|  | NM452 | 3 | NA** | 1817 (10 ng/ml) | ND* | 18.9 | ND* |
|  | MC58 | 4 | <10 | ~10 (40 ng/ml) | <10 (JAR 5) | ~2 | 1 |
| 8047 (v.2) | 8047 | 2 | 78 | 6250 (40 ng/ml) | 1341 (JAR 13) | 80.1 | 17.2 |
|  | RM1090 | 3 | 33 | 1612 (40 ng/ml) | 419 (JAR 31) | 48.8 | 12.7 |
|  | RM1090 | 3 | NA** | 804 (10 ng/ml) | ND* | 24.4 | ND* |

*ND, not done; **NA, not applicable
¶Chosen to bind to fHbp in the target strain

Example 7

Synthesis of KLH-Conjugated Peptides

JAR 4-reactive mimetic peptides were identified from phage display peptide libraries. The peptides contained DHK residues but had different flanking amino acid residues than those of the region of fHbp containing the native JAR 4 epitope. Epitope expressed by the phage peptide mimetics can be a good and stable immunogen. Serum antibodies elicited by peptide mimetics of JAR 4 can also be used to cooperate with polyclonal antibodies elicited by recombinant protein vaccines and augment serum bactericidal activity.

Phage peptide sequences 1 through 4 were identified through phage display experiments based on binding with anti-fHbp JAR 4 (Table 4). Negative control peptides include the following: 1) A peptide derived from the native fHbp sequence (peptide ID 1; gene from strain MC58) that included the JAR 4 consensus sequence DHK, which was shown to be necessary but not sufficient for the JAR 4 epitope; 2) A native fHbp peptide sequence from that region of fHbp molecule that was scrambled using the Shuffle Protein program at bioinformatics.org/sms2/shuffle_protein.html; 3) A peptide referred to as "Wyeth F82-E101", which was derived from another native fHbp amino acid sequence and was reported to inhibit binding of a broadly cross-reactive anti-fHbp mAb; 4) a peptide referred to as PorA P1.2, which was derived from loop 4 of PorA VR2, strain 2996 (Granoff D M et al. 2001 J. Immunol. 167:3487-3496) and reacts with a serosubtype-specific anti-P1.2 monoclonal antibody, and 5) a peptide referred to as "GNA 33", which is a mimetic of PorA P1.2 (Granoff D M et al. 2001 J. Immunol. 167:3487-3496).

The peptides (Table 4) were synthesized and conjugated to keyhole limpet hemocyanin (KLH) by a commercial supplier (Genscript Corp.). All of the JAR 4 peptides contained phage-encoded amino-terminal residues, AEGEF (SEQ ID NO: 4) and carboxyl-terminal residues, DPAK (SEQ ID NO: 5), which flanked the variable peptides. A cysteine (C) residue was added to the carboxyl-terminus to allow thiol coupling to KLH. The control peptides also contained the phage derived carboxyl-terminal residues, DPAK (SEQ ID NO: 6) and the additional C.

TABLE 4

JAR 4-derived and control peptides.

| Peptide | Sequence* | SEQ ID NO: | Yield (mg) | Purity (%) |
|---|---|---|---|---|
| JAR 4 phage 1 | AEGEFHDHKTQLDPDPAKC | 36 | 4.0 | 96.9 |
| JAR 4 phage 2 | AEGEFWTLAVFDHKAQTGDPAKC | 37 | 4.0 | 92.0 |
| JAR 4 phage 3 | AEGEFHDHKLEGTEDPAKC | 38 | 4.0 | 89.1 |
| JAR 4 phage 4** | AEGEFCGGVYDDKTGCAPDPAKC | 39 | 4.0 | 75.6 |
| JAR 4 native | ALTAPLDHKDKGLQSDPAKC | 40 | 4.0 | 80.8 |
| JAR 4 scrambled | TKDDPLKQHLALSAGDPAKC | 41 | 4.0 | 91.0 |
| Wyeth F82-E101 | FDFIRQIEVDGQLITLESGEDPAKC | 42 | 2.0 | 85.4 |
| PorA P1.2 | HFVQQTPQSQDPAKC | 43 | 3.0 | 81.9 |
| GNA 33 | AQAFQTPVHSDPAKC | 44 | 3.0 | 91.5 |

*Residues identified as JAR 4 consensus binding sequence shown in bold.
**Cyclic peptide containing disulfide bond between residues 6 and 16.

Example 8

Characterization of the Peptide-KLH Vaccines

The ability of anti-fHbp mAb JAR 4 to bind to the KLH-conjugated peptides was determined by a direct binding ELISA. ELISA plates were coated with 100 µl per well of a 2 µg/ml (peptide concentration) solution at 4° C. overnight. The following morning, the plates were washed and then blocked with PBS containing 1% BSA. The plates were washed and incubated with serial dilutions of mAb JAR 4 or, as a control, anti-fHbp JAR 5 or anti-PorA P1.2 mAb. After incubation (1 hour at room temperature), the plates were washed and incubated with anti-mouse IgG conjugated either with alkaline phosphatase or IRDye 800CW (1:1000). The alkaline phosphatase was detected at 420 nm wavelength after 30 min incubation with phosphatase substrate (1 mg/ml) and the IRDye was detected at 800 nm wavelength.

Figure 10:
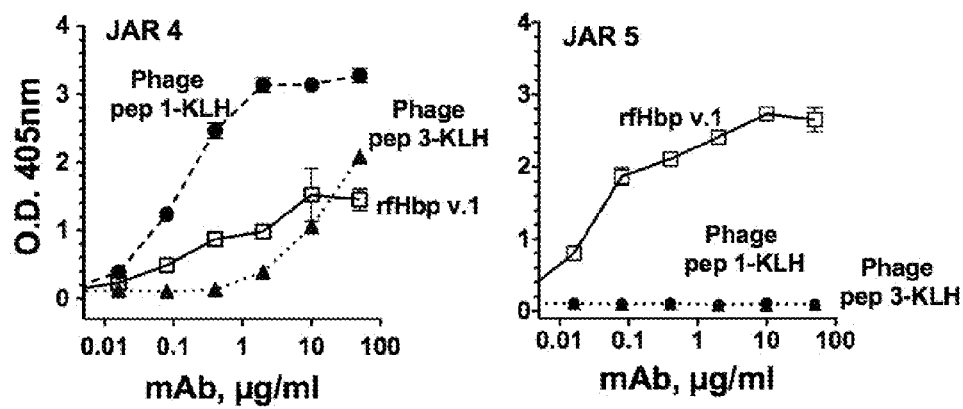
FIG. 10 presents graphs showing the concentration-dependent binding of JAR 4 to KLH-conjugated phage peptides and variant 1 fHbp, while JAR 5 does not bind significantly to the phage peptides.

By ELISA, JAR 4 reacted with all three KLH-conjugated JAR 4 phage peptides tested (phage 1, 2, and 3; Table 5). None of the JAR 4 peptides showed significant binding to control mAbs, anti-fHbp JAR 5 or anti-PorA P1.2. Representative data on concentration-dependent binding of JAR 4 to JAR 4 KLH-conjugated phage peptides 1 and 3 are shown are shown in FIG. 10 (left panel). There was no detectable binding of JAR 5 to these conjugates (right panel).

TABLE 5

Summary of mAb binding to KLH-conjugated peptides by ELISA.

| | mAb Reactivity* | | |
|---|---|---|---|
| Peptide | JAR 4 | JAR 5 | P1.2 |
| JAR 4 Phage 1 | ++ | − | − |
| JAR 4 Phage 2 | ++ | ND | − |
| JAR 4 Phage 3 | + | − | ND |
| JAR 4 Native | − | − | ND |
| JAR 4 Scrambled | − | − | − |
| PorA P1.2 | − | ND | + |
| GNA 33 | − | ND | + |

++, 50% of maximal binding at < 1 µg/ml;
+, 50% of maximal binding at 1-10 µg/ml;
−, no detectable binding at 50 µg/ml.
ND, not done

Example 9

Peptide Immunogenicity in Mice

Groups of mice will be immunized with 20 µg (peptide content) of KLH-conjugated peptide. All vaccines were mixed with Freund's Complete Adjuvant (FCA) for the first dose and incomplete (ICA) for the second and third doses. The vaccines will be administered IP at a three-weekly intervals. Additional groups of control mice will receive either two injections of 20 µg of recombinant fHbp (variant 1) per dose with adjuvant or adjuvant alone. Final blood samples for serologic analyses will be obtained by cardiac puncture three weeks after dose 3.

TABLE 6

Mouse immunogenicity study.

| Group | Immunogen | ADJUVANT |
|---|---|---|
| 1 | None | FCA/ICA |
|   | KLH-conjugated peptides | |
| 2 | JAR 4 Scrambled | FCA/ICA |
| 3 | JAR 4 Native | |
| 4 | JAR 4 Phage 1 | |
| 5 | JAR 4 Phage 2 | FCA/ICA |
| 6 | JAR 4 Phage 3 | |
| 7 | JAR 4 Phage 4 | |
| 8 | PorA P1.2 | |
| 9 | GNA 33 | |
| 10 | Wyeth F82-E101 | |
|   | Lauroyl-peptides | |
| 11 | JAR 4 Scrambled | OMV |
| 12 | JAR 4 phage 3 | |
| 13 | JAR 4 phage 4 | |
|   | Recombinant Protein | |
| 14 | fHbp peptide ID 1, variant 1 | FCA/ICA |

FCA/ICA in the table above refers to Freund's complete adjuvant for the first dose followed by incomplete adjuvant for doses 2 and 3. Peptides designated as lauroyl-peptides in the table above are synthetic peptides with an N-terminal cysteine-tyrosine-glycine-glycine (CYGG) linker (SEQ ID NO:74), conjugated with lauroyl group as previously described (Lowell, Ballou et al., Science, 1988). OMV in the table above refers to meningococcal outer membrane vesicles prepared as described in Lowell et al. (1988) *J. Exp. Med.* 167:658-63 and in Moe G R et al. (2002) *Infect. Immun.* 70:6021.

Example 10

Assessment of Serum Antibody Responses to Peptide-KLH Conjugate Vaccines

Responses Against Homologous Peptides.

Binding of pools of mouse antiserum from the immunization experiment described in Table 6 are tested against the homologous peptides. To test peptide-specific responses, the peptides listed in Table 4 are resynthesized with an amino-terminal biotin modification. ELISA plates are to be sensitized with streptavidin (100 µl of a 2 µg/ml solution in PBS).

Responses Against Purified Recombinant fHbp.

To test whether the JAR 4 epitope mimetic peptides elicited antibody that cross-reacted with fHbp, ELISAs are performed with fHbp protein immobilized on the plate. The antibody reactivity is tested against recombinant fHbp expressed from the genes from strains MC58 (peptide ID 1) and RM1090 (peptide ID 22), which express the JAR 4 epitope, and from strains M1239 (peptide ID 28) and Nm452 (peptide ID number 15), which does not express the epitope.

Ability of Serum Anti-Peptide Antibodies to Enhance Serum Bactericidal Activity.

The ability of sera from mice immunized with the different peptide-KLH conjugate vaccines to augment human complement-mediated bactericidal activity of sera from mice immunized with recombinant protein vaccines is tested as described above for JAR 4 augmentation of bactericidal activity.

Example 11

Assessment of Peptide Immunogenicity and Serum Antibody Responses to Peptide Modified with a Fatty Acid Among the peptides tested may also be those that are modified at the N-terminus with a fatty acid (e.g. lauroyl group), optionally conjugated through a linker. These N-terminally modified peptides may be administered as complexed to OMV vaccine as an adjuvant.

Responses Against Homologous Peptides.

Binding of pools of mouse antiserum from mice immunized with such modified peptides are tested against the homologous peptides. To test peptide-specific responses, the peptides listed in Table 4 may be synthesized with a lauroyl group. ELISA plates are to be sensitized with streptavidin (100 µl of a 2 µg/ml solution in PBS).

Responses Against Purified Recombinant fHbp.

To test whether the JAR 4 epitope mimetic peptides that are modified with a lauroyl group elicited antibody that cross-reacted with fHbp, ELISAs are performed with fHbp protein immobilized on the plate. The antibody reactivity is tested against recombinant fHbp expressed from the genes from strains MC58 (peptide ID 1) and RM1090 (peptide ID 22), which express the JAR 4 epitope, and from strains M1239 (peptide ID 28) and Nm452 (peptide ID number 15), which does not express the epitope.

Ability of Serum Anti-Peptide Antibodies to Enhance Serum Bactericidal Activity.

The sera from mice immunized with the different peptide vaccines in which the peptide contains an addition of lauroyl group at the N-terminus are tested for their ability to augment human complement-mediated bactericidal activity of sera from mice immunized with recombinant protein vaccines.

ATCC Deposit

Hybridomas producing the JAR 4, JAR 5, JAR 11, and JAR 32 monoclonal antibodies were deposited under the terms of the Budapest Treaty with the American Type Culture Collection, 10801 University Blvd., Manassas, Va. 20110-2209, USA (ATCC) on the date indicated in the table below, and were assigned the designations set out in the table below.

| ATCC Deposit No. (Deposit Date) | Material Deposited |
|---|---|
| PTA-8943 (Feb. 7, 2008) | Hybridoma producing JAR 4 Monoclonal Antibody |
| PTA-8941 (Feb. 7, 2008) | Hybridoma producing JAR 5 Monoclonal Antibody |
| PTA-8940 (Feb. 7, 2008) | Hybridoma producing JAR 10 Monoclonal Antibody |
| PTA-8938 (Feb. 7, 2008) | Hybridoma producing JAR 11 Monoclonal Antibody |
| PTA-8942 (Feb. 7, 2008) | Hybridoma producing JAR 32 Monoclonal Antibody |
| PTA-8939 (Feb. 7, 2008) | Hybridoma producing JAR 33 Monoclonal Antibody |

It should be noted that JAR 5 mAb specifically binds to an epitope that at least partially overlaps with the epitope specifically bound by JAR 3 mAb, and that JAR 32 mAb specifically binds to an epitope that at least partially overlaps with the epitope specifically bounds by JAR 35 mAb.

These deposits were made under the provisions of the Budapest Treaty on the International Recognition of the Deposit of Microorganisms for the Purpose of Patent Procedure and the Regulations there under (Budapest Treaty). This assures maintenance of a viable culture of the deposit for 30 years from the date of deposit and for at least five (5) years after the most recent request for the furnishing of a sample of the deposit received by the depository. The deposits will be made available by ATCC under the terms of the Budapest Treaty, and subject to an agreement between Children's Hospital & Research Center at Oakland and the ATCC (the assignee of the present application) which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 8860G 638).

The assignee(s) of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

What is claimed is:

1. An isolated JAR 4 epitope-containing peptide of at least 9 amino acids in length and comprising the sequence:

$$DX_1X_2$$

wherein $X_1$ is histidine (H) or aspartic acid (D);

$X_2$ is lysine (K) or arginine (R);

the aspartic acid residue (D) of the $DX_1X_2$ sequence does not contain an N-terminal amino group;

the peptide contains at least 3 amino acid residues positioned immediately C-terminal to the $X_2$, wherein the at least 3 amino acid residues are selected from:

| | |
|---|---|
| LEGTE, | (SEQ ID NO: 1) |
| TGCA, | (SEQ ID NO: 2) |
| TQL, | |
| AQT, | |
| SGC, | |
| TANQ, | (SEQ ID NO: 3) |
| IWP, | |
| HML, and | |
| HGF, | | with the proviso that when the at least 3 amino acid residues are TANQ (SEQ ID NO:3), the peptide comprises a histidine (H) immediately N-terminal to the aspartic acid residue (D) of the $DX_1X_2$ sequence, and when the at least 3 amino acid residues are TGCA (SEQ ID NO:2), the peptide comprises a tyrosine (Y) immediately N-terminal to the aspartic acid residue (D) of the $DX_1X_2$ sequence;

the peptide does not comprise a full-length A domain of a factor H binding protein; and the peptide is specifically bound by JAR 4 monoclonal antibody secreted by the hybridoma deposited as ATCC Accession No. PTA-8943.

2. The isolated JAR 4 epitope-containing peptide of claim 1, wherein the $X_1$ is histidine (H) and the $X_2$ is lysine (K).

3. The isolated JAR 4 epitope-containing peptide of claim 2, wherein the at least 3 amino acid residues are LEGTE (SEQ ID NO:1), TQL, AQT, TANQ (SEQ ID NO:3), or HGF.

4. The isolated JAR 4 epitope-containing peptide of claim 1, wherein the $X_1$ is aspartic acid (D) and the $X_2$ is lysine (K).

5. The isolated JAR 4 epitope-containing peptide of claim 4, wherein the at least 3 amino acid residues are TGCA (SEQ ID NO: 2).

6. The isolated JAR 4 epitope-containing peptide of claim 1, wherein the $X_1$ is histidine (H) and the $X_2$ is arginine (R).

7. The isolated JAR 4 epitope-containing peptide of claim 6, wherein the at least 3 amino acid residues are SGC, IWP, or HML.

8. An isolated peptide of at least 9 amino acids in length, and comprising at least 7 contiguous amino acid residues of an amino acid sequence of:

| | |
|---|---|
| H D H K L E G T E, | (SEQ ID NO: 14) |
| C G G V Y D D K T G C A, | (SEQ ID NO: 15) |
| H D H K T Q L D P, | (SEQ ID NO: 16) |
| W T L A V F D H K A Q T, | (SEQ ID NO: 17) |
| G C M G Y D H R S G C V, | (SEQ ID NO: 18) |
| F H D H K T A N Q, | (SEQ ID NO: 19) |

-continued

```
          H D H R I W P L D V T A,  (SEQ ID NO: 21)
          K D H R H M L W P E E S,  (SEQ ID NO: 25)
or
          H D H K G F Q E P A S,    (SEQ ID NO: 29)
```
wherein
the peptide contains the DHK, DDK, or DHR sequence,
the DHK, DDK, or DHR sequence does not contain an N-terminal amino group when present at the peptide N-terminus; and
the peptide is specifically bound by JAR 4 monoclonal antibody secreted by the hybridoma deposited as ATCC Accession No. PTA-8943.

9. An isolated peptide of at least 9 amino acids in length and comprising the contiguous amino acid sequence of:

```
                                   (SEQ ID NO: 22)
          N D E R Q M S D W Y R A,
or
                                   (SEQ ID NO: 23)
          H V H R G S Q G G Q R Q.
```

10. An isolated peptide of at least 9 amino acids in length and comprising the contiguous amino acid sequence of:

```
                                   (SEQ ID NO: 20)
          W R W C G F E R C P E G, (SEQ ID NO: 30)
          S D W G W G G R A E Q H, (SEQ ID NO: 31)
          V G W C G F E R C S S A, (SEQ ID NO: 24)
          L E W C G F S R C E V G, (SEQ ID NO: 26)
          L C Q E R L S Q R C G V, (SEQ ID NO: 27)
          W V L C G Q G C G G T A,
or
                                   (SEQ ID NO: 28)
          R C Q V Q V M V L C A L.
```

11. The isolated peptide of claim 1 wherein said peptide is conjugated to a fatty acid residue at the N-terminus.

12. An isolated nucleic acid encoding the peptide according to claim 1.

13. An immunogenic composition comprising:
the peptide according to claim 1; and
a pharmaceutically acceptable excipient.

14. The immunogenic composition of claim 13, wherein the peptide is coupled to a carrier molecule.

15. The immunogenic composition of claim 13, wherein the composition comprises an adjuvant.

16. The immunogenic composition of claim 13, further comprising a polypeptide comprising an amino acid sequence of a factor H binding protein (fHbp) that is specifically bound by at least one of the monoclonal antibodies JAR 3, JAR 5, JAR 11, and JAR 13.

17. The immunogenic composition of claim 13, wherein said peptide is conjugated to a fatty acid residue at the N-terminus.

18. The immunogenic composition of claim 17, wherein said fatty acid residue comprises a lauroyl group.

19. The immunogenic composition of claim 13, wherein said composition comprises outer membrane vesicles, membrane vesicles, or a mixture of outer membrane vesicles and membrane vesicles obtained from *Neisseria meningitidis*.

20. The immunogenic composition of claim 13, wherein said composition comprises an fHbp.

21. The immunogenic composition of claim 13, wherein said composition comprises the r3C vaccine.

22. A method of inducing an immune response to *Neisseria meningitidis* in a subject comprising:
administering the immunogenic composition according to claim 13 to the subject in an amount effective to elicit production of antibodies to the peptide in the subject.

23. A method of inducing an immune response to *Neisseria meningitidis* in a subject, comprising:
administering to the subject an immunogenic composition comprising a JAR 4 epitope-containing peptide of at least 9 amino acids in length and comprising the sequence:

$$DX_1X_2$$

wherein
$X_1$ is histidine (H) or aspartic acid (D);
$X_2$ is lysine (K) or arginine (R);
the aspartic acid residue (D) of the $DX_1X_2$ sequence does not contain an N-terminal amino group;
the peptide does not comprise a full-length A domain of a factor H binding protein;
the peptide is specifically bound by JAR 4 monoclonal antibody secreted by the hybridoma deposited as ATCC Accession No. PTA-8943; and
wherein said administering is effective to elicit production of antibodies to the peptide in the subject.

24. The method of claim 23, wherein the $X_1$ is histidine (H) and the $X_2$ is lysine (K).

25. The method of claim 24, wherein the peptide comprises the amino acid sequence of LEGTE (SEQ ID NO:1), TQL, AQT, TANQ (SEQ ID NO:3), or HGF immediately C-terminal to the $X_2$.

26. The method of claim 23, wherein the $X_1$ is aspartic acid (D) and the $X_2$ is lysine (K).

27. The method of claim 24, wherein the peptide comprises the amino acid sequence of TGCA (SEQ ID NO: 2) immediately C-terminal to the $X_2$.

28. The method of claim 23, wherein the $X_1$ is histidine (H) and the $X_2$ is arginine (R).

29. The method of claim 28, wherein the peptide comprises the amino acid sequence of SGC, IWP, or HML immediately C-terminal to the $X_2$.

30. The method of claim 28, wherein said peptide is conjugated to a fatty acid residue at the N-terminus.

31. A method of making an immunogenic composition against *Neisseria meningitidis* comprising combining the isolated peptide of claim 1, with a factor H binding protein.

32. The method of claim 31, wherein said factor H binding protein is expressed by a *Neisseria meningitidis* cell that is genetically modified to express the factor H binding protein.

33. The method of claim 32, wherein said *Neisseria meningitidis* cell is genetically modified to attenuate the expression of lpxL1 gene.

34. The method of claim 33, comprising combining said isolated peptide with vesicles obtained from a *Neisseria meningitidis* cell that is genetically modified to express factor H binding protein.

35. The method of claim 34, wherein said vesicles are treated with a detergent.

36. The method of claim 31, wherein said peptide is conjugated to a fatty acid residue at the N-terminus.

37. The immunogenic composition of claim 11, wherein said peptide is conjugated to a fatty acid residue at the N-terminus through a linker.

38. The immunogenic composition of claim 17, wherein said peptide is conjugated to a fatty acid residue at the N-terminus through a linker.

39. The method of claim 30, wherein said peptide is conjugated to a fatty acid residue at the N-terminus through a linker.

40. The method of claim 36, wherein said peptide is conjugated to a fatty acid residue at the N-terminus through a linker.

* * * * *

SEQUENCE LISTING

```
<160> NUMBER OF SEQ ID NOS: 74

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Leu Glu Gly Thr Glu
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 2

Thr Gly Cys Ala
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Thr Ala Asn Gln
1

<210> SEQ ID NO 4
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 4

Leu Asp His Lys Asp Lys Gly
1               5
```

```
<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 5

Phe Leu Leu Ala Val
 1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 6

Gly Ser Gly Gly Ser
 1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 7

Gly Gly Gly Ser
 1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 8

Gly Gly Ser Gly
 1

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Gly Gly Ser Gly Gly
 1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Gly Ser Gly Ser Gly
 1               5

<210> SEQ ID NO 11
```

```
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Gly Ser Gly Gly Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 12

Gly Gly Gly Ser Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 13

Gly Ser Ser Ser Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

His Asp His Lys Leu Glu Gly Thr Glu
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 15

Cys Gly Gly Val Tyr Asp Asp Lys Thr Gly Cys Ala
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 16

His Asp His Lys Thr Gln Leu Asp Pro
1               5

<210> SEQ ID NO 17
<211> LENGTH: 12
<212> TYPE: PRT
```

```
<213> ORGANISM: Artificial Sequence
<220> FEATURE:
<223> OTHER INFORMATION: Synthetic Peptide

<400> SEQUENCE: 17

Trp Thr Leu Ala Val Phe Asp His Lys Ala Gln Thr
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 18

Gly Cys Met Gly Tyr Asp His Arg Ser Gly Cys Val
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 19

Phe His Asp His Lys Thr Ala Asn Gln
1               5

<210> SEQ ID NO 20
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 20

Trp Arg Trp Cys Gly Phe Glu Arg Cys Pro Glu Gly
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 21

His Asp His Arg Ile Trp Pro Leu Asp Val Thr Ala
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 22

Asn Asp Glu Arg Gln Met Ser Asp Trp Tyr Arg Ala
1               5                   10

<210> SEQ ID NO 23
<211> LENGTH: 12
<212> TYPE: PRT
<213> ORGANISM: Artificial Sequence
<220> FEATURE:
```

```
<223> OTHER INFORMATION: Synthetic Peptide

<400> SEQUENCE: 23

His Val His Arg Gly Ser Gln Gly Gly Gln Arg Gln
 1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 24

Leu Glu Trp Cys Gly Phe Ser Arg Cys Glu Val Gly
 1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 25

Lys Asp His Arg His Met Leu Trp Pro Glu Glu Ser
 1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 26

Leu Cys Gln Glu Arg Leu Ser Gln Arg Cys Gly Val
 1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 27

Trp Val Leu Cys Gly Gln Gly Cys Gly Gly Thr Ala
 1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 28

Arg Cys Gln Val Gln Val Met Val Leu Cys Ala Leu
 1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic Peptide
```

```
<400> SEQUENCE: 29

His Asp His Lys His Gly Phe Gln Glu Pro Ala Ser
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 30

Ser Asp Trp Gly Trp Gly Gly Arg Ala Glu Gln His
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 31

Val Gly Trp Cys Gly Phe Glu Arg Cys Ser Ser Ala
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 32

Ala Asp Ala Leu Thr Ala Pro Leu Asp His Lys Asp Lys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 33

Asp His Lys Asp Lys Gly Leu Gln Ser Leu Thr Leu Asp
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 34

Ala Glu Gly Glu Phe
1               5

<210> SEQ ID NO 35
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 35
```

```
Asp Pro Ala Lys
  1

<210> SEQ ID NO 36
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 36

Ala Glu Gly Glu Phe His Asp His Lys Thr Gln Leu Asp Pro Asp Pro
  1               5                  10                  15

Ala Lys Cys

<210> SEQ ID NO 37
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 37

Ala Glu Gly Glu Phe Trp Thr Leu Ala Val Phe Asp His Lys Ala Gln
  1               5                  10                  15

Thr Gly Asp Pro Ala Lys Cys
                 20

<210> SEQ ID NO 38
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 38

Ala Glu Gly Glu Phe His Asp His Lys Leu Glu Gly Thr Glu Asp Pro
  1               5                  10                  15

Ala Lys Cys

<210> SEQ ID NO 39
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 39

Ala Glu Gly Glu Phe Cys Gly Gly Val Tyr Asp Asp Lys Thr Gly Cys
  1               5                  10                  15

Ala Pro Asp Pro Ala Lys Cys
                 20

<210> SEQ ID NO 40
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 40

Ala Leu Thr Ala Pro Leu Asp His Asp Lys Gly Leu Gln Ser Asp
  1               5                  10                  15

Pro Ala Lys Cys
         20
```

```
<210> SEQ ID NO 41
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 41

Thr Lys Asp Asp Pro Leu Lys Gln His Leu Ala Leu Ser Ala Gly Asp
 1               5                  10                  15

Pro Ala Lys Cys
            20

<210> SEQ ID NO 42
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 42

Phe Asp Phe Ile Arg Gln Ile Glu Val Asp Gly Gln Leu Ile Thr Leu
 1               5                  10                  15

Glu Ser Gly Glu Asp Pro Ala Lys Cys
            20                  25

<210> SEQ ID NO 43
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 43

His Phe Val Gln Gln Thr Pro Gln Ser Gln Asp Pro Ala Lys Cys
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 44

Ala Gln Ala Phe Gln Thr Pro Val His Ser Asp Pro Ala Lys Cys
 1               5                  10                  15

<210> SEQ ID NO 45
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 45
cacgatcata aattagaagg cacggag                                        27

<210> SEQ ID NO 46
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 46
```

-continued tgtggcgggg tctacgacga caagacgggg tgtgcg        36

<210> SEQ ID NO 47
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 47
catgaccaca agacccagct cgacccg        27

<210> SEQ ID NO 48
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 48
tggaccctgg cggtgttcga ccacaaagcg cagacc        36

<210> SEQ ID NO 49
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 49
gggtgtatgg gctacgacca caggtcgggc tgtgtg        36

<210> SEQ ID NO 50
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 50
tttcatgacc acaaaactgc caatcag        27

<210> SEQ ID NO 51
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 51
tggaggtggt gtggcttcga gcgctgtccc gagggc        36

<210> SEQ ID NO 52
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 52
cacgaccacc gtatctggcc gctggacgtg accgcg        36

<210> SEQ ID NO 53
<211> LENGTH: 36
<212> TYPE: DNA
<213> ORGANISM: Artificial Sequence

```
<220> FEATURE:
<223> OTHER INFORMATION: Synthetic Polynucleotide

<400> SEQUENCE: 53
aacgacgaac gtcagatgtc cgactggtac cgtgcg                                36

<210> SEQ ID NO 54
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 54
cacgtccacc gtggttcgca gggtggtcag cgtcag                                36

<210> SEQ ID NO 55
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 55
ctcgagtggt gtggcttcag caggtgtgag gtcggc                                36

<210> SEQ ID NO 56
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 56
aaagaccacc gtcacatgct gtggccggaa gaatcc                                36

<210> SEQ ID NO 57
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 57
ctctgtcagg agcggctctc ctagaggtgt ggggtg                                36

<210> SEQ ID NO 58
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 58
tgggtgttgt gtggctaggg ctgtggggc acggcg                                 36

<210> SEQ ID NO 59
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 59
aggtgttagg tccaggtcat ggtgctgtgt gcgctc                                36
```

<210> SEQ ID NO 60
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 60
cacgaccaca aacacggttt ccaggaaccg gcgtcc                36

<210> SEQ ID NO 61
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 61
tccgactggg gttggggtgg ccgtgcggaa cagcac                36

<210> SEQ ID NO 62
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 62
gtggggtggt gtggcttcga gcggtgttcg tcggcg                36

<210> SEQ ID NO 63
<211> LENGTH: 274
<212> TYPE: PRT
<213> ORGANISM: Neisseria menigitidis

<400> SEQUENCE: 63

Met Asn Arg Thr Ala Phe Cys Cys Leu Ser Leu Thr Thr Ala Leu Ile
 1               5                  10                  15

Leu Thr Ala Cys Ser Ser Gly Gly Gly Val Ala Ala Asp Ile Gly
                20                  25                  30

Ala Gly Leu Ala Asp Ala Leu Thr Ala Pro Leu Asp His Lys Asp Lys
            35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
            100                 105                 110

Gly Glu Phe Gln Val Tyr Lys Gln Ser His Ser Ala Leu Thr Ala Phe
        115                 120                 125

Gln Thr Glu Gln Ile Gln Asp Ser Glu His Ser Gly Lys Met Val Ala
    130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
                165                 170                 175

Gly Ser Asp Asp Ala Gly Gly Lys Leu Thr Tyr Thr Ile Asp Phe Ala
            180                 185                 190

Ala Lys Gln Gly Asn Gly Lys Ile Glu His Leu Lys Ser Pro Glu Leu

```
                     195                 200                 205
Asn Val Asp Leu Ala Ala Asp Ile Lys Pro Asp Gly Lys Arg His
            210                 215                 220
Ala Val Ile Ser Gly Ser Val Leu Tyr Asn Gln Ala Glu Lys Gly Ser
225                 230                 235                 240
Tyr Ser Leu Gly Ile Phe Gly Gly Lys Ala Gln Glu Val Ala Gly Ser
                245                 250                 255
Ala Glu Val Lys Thr Val Asn Gly Ile Arg His Ile Gly Leu Ala Ala
            260                 265                 270
Lys Gln

<210> SEQ ID NO 64
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 64

Thr Ala Pro Leu Asp His Lys Asp Lys Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 65

Thr Ala Pro Leu Ala Ala Lys Asp Lys Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 66

Thr Ala Pro Leu Asp Ala Lys Asp Lys Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 67

Thr Ala Pro Leu Asp His Ala Asp Lys Gly
1               5                   10

<210> SEQ ID NO 68
<211> LENGTH: 61
<212> TYPE: PRT
<213> ORGANISM: Artificial Sequence
<220> FEATURE:
<223> OTHER INFORMATION: Synthetic Peptide

<400> SEQUENCE: 68

Cys Ser Ser Gly Gly Gly Gly Val Ala Ala Asp Ile Gly Ala Gly Leu
1               5                   10                  15
```

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp
            50                  55                  60

<210> SEQ ID NO 69
<211> LENGTH: 61
<212> TYPE: PRT
<213> ORGANISM: Artificial Sequence
<220> FEATURE:
<223> OTHER INFORMATION: Synthetic Peptide

<400> SEQUENCE: 69

Cys Ser Ser Gly Gly Gly Gly Val Ala Ala Asp Ile Gly Ala Gly Leu
 1               5                  10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp
            50                  55                  60

<210> SEQ ID NO 70
<211> LENGTH: 69
<212> TYPE: PRT
<213> ORGANISM: Artificial Sequence
<220> FEATURE:
<223> OTHER INFORMATION: Synthetic Peptide

<400> SEQUENCE: 70

Cys Ser Ser Gly Gly Gly Gly Ser Gly Gly Gly Val Ala Ala Asp
 1               5                  10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
            35                  40                  45

Gly Thr Leu Thr Leu Ser Ala Gln Gly Ala Glu Lys Thr Phe Lys Ala
            50                  55                  60

Gly Asp Lys Asp Asn
65

<210> SEQ ID NO 71
<211> LENGTH: 4
<212> TYPE: PRT
<213> ORGANISM: Artificial Sequence
<220> FEATURE:
<223> OTHER INFORMATION: Synthetic peptide

<400> SEQUENCE: 71

Trp Cys Gly Phe
 1

<210> SEQ ID NO 72
<211> LENGTH: 6
<212> TYPE: PRT
<213> ORGANISM: Artificial Sequence
<220> FEATURE:
<223> OTHER INFORMATION: Synthetic peptide

<400> SEQUENCE: 72

```
Trp Cys Gly Phe Glu Arg
 1               5

<210> SEQ ID NO 73
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: NON_CONS
<222> LOCATION: (5)...(6)

<400> SEQUENCE: 73

Met Val Ala Ala Asp Gly Leu Ala Ala Lys Gln
 1               5                  10

<210> SEQ ID NO 74
<211> LENGTH: 4
<212> TYPE: PRT
<213> ORGANISM: Artificial Sequence
<220> FEATURE:
<223> OTHER INFORMATION: Synthetic peptide

<400> SEQUENCE: 74

Cys Tyr Gly Gly
 1
```